(12) United States Patent
El-Deiry et al.

(10) Patent No.: US 10,322,123 B2
(45) Date of Patent: Jun. 18, 2019

(54) COMPOUND FOR ANTI-CANCER THERAPY THAT ACTS BY TARGETING GOF MUTANT P53 AND STIMULATES P73 TO RESTORE THE P53 PATHWAY SIGNALING

(71) Applicant: The Penn State Research Foundation, University Park, PA (US)

(72) Inventors: Wafik S. El-Deiry, Bryn Mawr, PA (US); Shengliang Zhang, Jenkintown, PA (US)

(73) Assignee: THE PENN STATE RESEARCH FOUNDATION, University Park, PA (US)

( * ) Notice: Subject to any disclaimer, the term of this patent is extended or adjusted under 35 U.S.C. 154(b) by 0 days.

(21) Appl. No.: 15/514,623

(22) PCT Filed: Sep. 29, 2015

(86) PCT No.: PCT/US2015/052791
§ 371 (c)(1),
(2) Date: Mar. 27, 2017

(87) PCT Pub. No.: WO2016/053938
PCT Pub. Date: Apr. 7, 2016

(65) Prior Publication Data
US 2017/0209438 A1  Jul. 27, 2017

Related U.S. Application Data

(60) Provisional application No. 62/056,870, filed on Sep. 29, 2014.

(51) Int. Cl.
*A61K 31/496* (2006.01)
*C07D 307/71* (2006.01)

(52) U.S. Cl.
CPC .......... *A61K 31/496* (2013.01); *C07D 307/71* (2013.01)

(58) Field of Classification Search
CPC .................................................. A61K 31/496
See application file for complete search history.

(56) References Cited

U.S. PATENT DOCUMENTS

| 4,904,697 A | 2/1990 | Sunkara et al. |
| 6,602,879 B2 | 8/2003 | Murthy et al. |
| 8,138,356 B2 | 3/2012 | Chaudhary et al. |
| 2010/0047783 A1 | 2/2010 | El-Diery |

FOREIGN PATENT DOCUMENTS

| WO | 0146110 A2 | 6/2001 |
| WO | 03075943 A2 | 9/2003 |
| WO | 2007/039170 A1 | 4/2007 |
| WO | 2014022287 A1 | 2/2014 |

OTHER PUBLICATIONS

Pubchem, 2005, "Compound Summary for CID 5356520"; https://pubchem.ncbi.nlm.nih.gov/compound/5356520.
Bassett et al., "Structural and functional basis for therapeutic modulation of p53 signaling", Clin Cancer Res. Oct. 15, 2008;14(20):6376-86.
Bisso et al., "p73 as a Pharmaceutical Target for Cancer Therapy", Current Pharmaceutical Design, 2011, 17, 578-590.
Wang et al., "Small-molecule modulators of p53 family signaling and antitumor effects in p53-deficient human colon tumor xenografts", PNAS, 2006, 103: 11003-11008.
Hong et al., "Prodigiosin Rescues Deficient p53 Signaling and Antitumor Effects via Upregulating p73 and Disrupting Its Interaction with Mutant p53", Cancer Res, 2013, 74(4); 1153-65.
Xi M.-Y. et al. "Synthesis and bioevaluation of a series of IX-pyrone derivatives as potent activators of Nrf2/ARE pathway (part I)" 2013, Europ. J. Medicin. Chem., 66: 364-371.
Xian-Yu Z. et al. "A Preliminary Note on the Relationship between Structure and Antischistosomal Activity of Nitrofurazones" 1963, Acta Pharma. Sinica 10: 407-417.
Zhang Y. et al. "A New Chalcone Derivative (E)-3-(4-Methoxyphenyl)-2-methyl-1-(3,4,5-trimethoxyphenyl)prop-2-en-I-one Suppresses Prostate Cancer Involving p53-mediated Cell Cycle Arrests and Apoptosis" 2012, Anticancer Research 32: 3689-3698.
Vuyyuri S. B. et al. "Ascorbic Acid and a Cytostatic Inhibitor of Glycolysis Synergistically Induce Apoptosis in Non-Small Cell Lung Cancer Cells" 2013, PLOS One, 8: e67081.

*Primary Examiner* — Golam M Shameem
(74) *Attorney, Agent, or Firm* — Riverside Law LLP

(57) ABSTRACT

The invention includes compositions comprising NSC59984 or a derivative or analog thereof and a pharmaceutically acceptable carrier. The invention further includes methods of treating or preventing cancer in a subject, comprising the step of administering to the subject the compositions contemplated within the invention.

17 Claims, 9 Drawing Sheets

Specification includes a Sequence Listing.

SEQUENCE LISTING

<160> NUMBER OF SEQ ID NOS: 10

<210> SEQ ID NO 1
<211> LENGTH: 20
<212> TYPE: DNA
<213> ORGANISM: Artificial sequence
<220> FEATURE:
<223> OTHER INFORMATION: Chemically synthesized

<400> SEQUENCE: 1
gaggttggct ctgactgtac                                                  20

<210> SEQ ID NO 2
<211> LENGTH: 20
<212> TYPE: DNA
<213> ORGANISM: Artificial sequence
<220> FEATURE:
<223> OTHER INFORMATION: Chemically synthesized

<400> SEQUENCE: 2
tccgtcccag tagattacca                                                  20

<210> SEQ ID NO 3
<211> LENGTH: 18
<212> TYPE: DNA
<213> ORGANISM: Artificial sequence
<220> FEATURE:
<223> OTHER INFORMATION: Chemically synthesized

<400> SEQUENCE: 3
tgtccgtcag aacccatg                                                    18

<210> SEQ ID NO 4
<211> LENGTH: 20

```
<212> TYPE: DNA
<213> ORGANISM: Artificial sequence
<220> FEATURE:
<223> OTHER INFORMATION: Chemically synthesized

<400> SEQUENCE: 4
aaagtcgaag ttccatcgct                                              20

<210> SEQ ID NO 5
<211> LENGTH: 20
<212> TYPE: DNA
<213> ORGANISM: Artificial sequence
<220> FEATURE:
<223> OTHER INFORMATION: Chemically synthesized

<400> SEQUENCE: 5
gacgacctca acgcacagta                                              20

<210> SEQ ID NO 6
<211> LENGTH: 22
<212> TYPE: DNA
<213> ORGANISM: Artificial sequence
<220> FEATURE:
<223> OTHER INFORMATION: Chemically synthesized

<400> SEQUENCE: 6
aggagtccca tgatgagatt gt                                           22

<210> SEQ ID NO 7
<211> LENGTH: 20
<212> TYPE: DNA
<213> ORGANISM: Artificial sequence
<220> FEATURE:
<223> OTHER INFORMATION: Chemically synthesized

<400> SEQUENCE: 7
gcagagctgg aagtcgagtg                                              20

<210> SEQ ID NO 8
<211> LENGTH: 23
<212> TYPE: DNA
<213> ORGANISM: Artificial sequence
<220> FEATURE:
<223> OTHER INFORMATION: Chemically synthesized

<400> SEQUENCE: 8
gagcagaaga gtttggatat cag                                          23

<210> SEQ ID NO 9
<211> LENGTH: 19
<212> TYPE: DNA
<213> ORGANISM: Artificial sequence
<220> FEATURE:
<223> OTHER INFORMATION: Chemically synthesized

<400> SEQUENCE: 9
ctgggctaca ctgagcacc                                               19

<210> SEQ ID NO 10
<211> LENGTH: 21
<212> TYPE: DNA
<213> ORGANISM: Artificial sequence
<220> FEATURE:
<223> OTHER INFORMATION: Chemically synthesized

<400> SEQUENCE: 10
aagtggtcgt tgagggcaat g                                            21
```

COMPOUND FOR ANTI-CANCER THERAPY THAT ACTS BY TARGETING GOF MUTANT P53 AND STIMULATES P73 TO RESTORE THE P53 PATHWAY SIGNALING

CROSS REFERENCE TO RELATED APPLICATIONS

The present application claims priority from U.S. Provisional Application No. 62/056,870, filed Sep. 29, 2014, the entire disclosure of which is incorporated by reference herein as if set forth herein in its entirety.

STATEMENT REGARDING FEDERALLY SPONSORED RESEARCH OR DEVELOPMENT

This invention was made with government support under Grant No. CN043302 awarded by the National Institutes of Health. The government has certain rights in the invention.

BACKGROUND OF THE INVENTION

Tumor suppressor p53 protects cells from oncogenesis and promotes sensitivity to ant-cancer therapy. p53 protein expression remains low under basal conditions due to MDM2-mediated feedback inhibition and the E3 ubiquitin ligase activity of MDM2 (Wade M et al., Nat Rev Cancer 2013; 13: 83-96). Cellular stresses such as DNA damage or other cellular stress, hypoxia, viral infection or oncogenic transformation stimulate the p53 pathway by stabilizing p53 protein and by inducing its transcriptional activity (Vousden K H, et al. Cell 2009; 137: 413-31).

Active p53 up-regulates the expression of multiple genes, including p21 (el-Deiry W S, et al., Cell 1993; 75: 817-25), Puma (Hikisz P, et al., Cell Mol Biol Lett 2012; 17: 646-69) and DR5 (Wu G S, et al., Adv Exp Med Biol 2000; 465: 143-51), inducing cell cycle arrest, cell death and DNA repair processes to prevent cellular transformation and tumor development. Inactivation of p53 occurs most human tumors due to p53 mutation or down-regulation of p53 expression by various inhibitors, such as MDM2 or HPV E6 (Brooks C L, et al., Mol Cell 2006; 21: 307-15; Olivier M, et al., Cold Spring Harb Perspect Biol 2010; 2: a001008; and Havre P A, et al., Cancer Res 1995; 55: 4420-4). Deregulation of p53 represents a basic difference between normal and cancer cells.

Over two decades ago, wild-type p53 was shown to suppress colon cancer cell colony growth, despite their other genetic alterations including KRAS, PIK3CA and APC mutation as well as metastasis promoting genes (Baker S J, et al., Science 1990; 249: 912-5; and van Oijen M G, et al., Clin Cancer Res 2000; 6: 2138-45). Therefore, p53 pathway restoration remains an outstanding strategy for cancer therapy, and small molecules continue to represent a reasonable and potentially feasible strategy to achieve this goal.

Over 50% of human cancers harbor mutant p53, which inactivates p53 pathway signaling and its tumor suppressor function (van Oijen M G, et al., Clin Cancer Res 2000; 6: 2138-45). The vast majority of p53 mutations in human cancer are missense point mutations. Most mutations are clustered in the p53 DNA-binding domain, which causes mutant p53 to lose its DNA binding and transactivation capability leading to a failure to up-regulate p53 effector genes (Olivier M, et al., Cold Spring Harb Perspect Biol 2010; 2: a001008). p53 DNA mutations not only abrogate the p53 tumor suppressor function, but can also endow mutant p53 with a gain-of-function (GOF), rendering it a proto-oncogene (Muller P A, et al., Nat Cell Biol 2013; 15: 2-8; and Oren M, et al., Cold Spring Harb Perspect Biol 2010; 2: a001107). Delivery of mutant p53 into p53-null tumor cells was found to accelerate cancer development (Dittmer D, et al., Nat Genet 1993; 4: 42-6; and Olive K P, et al., Cell 2004; 119: 847-60), suggesting that GOF can exert oncogenic activity. One property of mutant p53 GOF is to form aberrant protein complexes with numerous interacting protein factors, including a subset of transcription factors such as SP1, NF-Y, p53, and p63/p73, to perturb their activities (Freed-Pastor W A, et al., Genes Dev 2012; 26: 1268-86). For example, inactive p73 may contribute to chemoresistance.

Many studies from animals and cell-based assays suggest that the GOF of mutant p53 contributes to tumorigenesis, tumor progression and resistance to therapy (Oren M, et al., Cold Spring Harb Perspect Biol 2010; 2: a001107). Knocking down mutant p53 has been found to sensitize cancer cells to chemotherapy (Li D, et al., Cell Death Differ 2011; 18: 1904-13; and Wang J, et al., J Cell Biochem 2011; 112: 509-19). Therefore, targeting mutant p53 is an attractive strategy to overcome drug resistance and to sensitize tumors to cancer therapy. This concept is particularly further developed and mechanistically explored in the present study with NSC59984.

Some small molecule compounds targeting mutant p53 have been selected based on putative conformational changes within mutant p53 to restore wild-type p53. For example, CP31398 (Foster B A, et al., Science 1999; 286: 2507-10), PRIMA-1 (Bykov V J, et al., Nat Med 2002; 8: 282-8) and NSC319726 (Yu X, et al., Cancer Cell 2012; 21: 614-25) have been proposed to cause a conformational shift from mutant to wild-type p53, reactivating p53 function in tumor suppression. Although several small molecules can restore the p53 pathway, the GOF of mutant p53 can remain in the tumor cell and can represent an obstacle to tumor suppression as well as therapeutic efficacy. Eliminating mutant p53 is an approach that we decided to pursue in an attempt to abolish the GOF properties of mutant p53 in tumor cells, and with the idea that mutant p53 may represent a challenge for the general approach to stimulate p73, given the ability of mutant p53 to quench the tumor suppressive activity of p73.

A major difference between wild-type and mutant p53 is that mutant p53 proteins are hyper-stabilized in cells. The molecular chaperones Hsp90 and Hsp70 play an important role in keeping mutant p53 protein stable by inhibiting MDM2 and CHIP (Li D, et al., Mol Cancer Res 2011; 9: 577-88). Few compounds have been reported to destabilize mutant p53, including 17AAG, Saha, gambogic acid and Arsenic (Li D, et al., Cell Death Differ 2011; 18: 1904-13; Wang J, et al., J Cell Biochem 2011; 112: 509-19; Li D, et al., Mol Cancer Res 2011; 9: 577-88; and Zhang Y, et al., J Biol Chem 2011; 286: 16218-28). HDAC inhibitors and gambogic acid have been reported to destabilize mutant p53 by activating MDM2 or CHIP (Li D, et al., Cell Death Differ 2011; 18: 1904-13; and Wang J, et al., J Cell Biochem 2011; 112: 509-19). However, those compounds are incapable of restoring the p53 pathway of mutant p53 in tumor cells, and they have many other targets and mechanisms, making them non-specific. Thus, small molecules with the dual capability to restore the p53 pathway and deplete mutant p53 GOF proteins represent a novel strategy for cancer therapy and appear desirable to pursue for further therapeutic development.

p73, a member of the p53 family, is a transcription factor with high structural and sequence homology with p53. p73 has been found to have similar functions as wild-type p53 (Melino G, et al., Nat Rev Cancer 2002; 2: 605-15). p73 can transactivate the vast majority of p53 transcriptional target genes by binding to their regulatory regions in the same manner as p53, including in heterologous complexes of p53:p73; thereby impacting on cell growth and cell death pathways (Lunghi P, et al., Clin Cancer Res 2009; 15: 6495-502). Knock-out of p73 contributes to tumor development, functionally implicating p73 as a tumor suppressor (Tomasini R, et al., Genes Dev 2008; 22: 2677-91). Unlike p53, p73 is rarely deleted or mutated in human cancer. p73 is activated by complex signaling pathways in mammalian cells under stress. For example, c-Abl phosphorylates p73 and p300 acetylates p73 in response to cellular stress or DNA damage (Conforti F, et al., Cell Death Dis 2012; 3: e285). Activated p73 induces apoptosis and enhances chemosensitivity. A large variety of chemotherapeutic agents, such as camptothecin, etoposide and cisplatin, can up-regulate p73 expression (Irwin M S, et al., Cancer Cell 2003; 3: 403-10). However, in mutant p53-expressing cancer cells, mutant p53 inhibits p73 activation by binding with p73 to form an inhibited complex with respect to the transactivation of target genes (Freed-Pastor W A, et al., Genes Dev 2012; 26: 1268-86). Inactivated p73 promotes chemoresistance. Therefore, p73 provides a legitimate and bona fide attractive target to restore the p53 pathway in cancer therapy. A peptide, 37AA, has been found to cause p73 dependent cancer cell apoptosis (Bell H S, et al., J Clin Invest 2007; 117: 1008-18). A small molecule, RETRA, was shown to release p73 by disturbing interaction of p73 and mutant p53 (Kravchenko J E, et al., Proc Natl Acad Sci USA 2008; 105: 6302-7). These studies support the strategy of bypassing dysfunctional p53 signaling in cancer therapy through stimulation of p73-dependent signaling, while at the same time attempting to eliminate mutant p53, as is reported here.

There is a need in the art for small molecule compounds that both destabilize mutant p53 and restore wild-type p53 pathway via the activation of p73 in cancer cells. The present invention addresses this unmet need.

SUMMARY OF THE INVENTION

The present invention relates to a pharmaceutical composition comprising a pharmaceutically acceptable carrier and a compound of formula (I) or a salt, solvate, or N-oxide thereof:

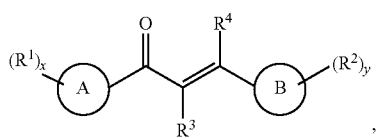

(I)

wherein in formula (I):

ring A is a monocyclic or bicyclic aryl, a monocyclic or bicyclic heteroaryl, or a monocyclic or bicyclic heterocyclyl ring, and wherein the aryl, heteroaryl, or heterocyclyl ring is optionally substituted with 0-5 $R^1$ groups;

ring B is a monocyclic or bicyclic aryl, a monocyclic or bicyclic heteroaryl, or a monocyclic or bicyclic heterocyclyl ring, and wherein the aryl, heteroaryl, or heterocyclyl ring is optionally substituted with 0-5 $R^2$ groups;

each occurrence of $R^1$ and $R^2$ are independently selected from the group consisting of —$C_1$-$C_6$ alkyl, —$C_1$-$C_6$ fluoroalkyl, —$C_1$-$C_6$ heteroalkyl, F, Cl, Br, I, —CN, —$NO_2$, —$OR^5$, —$SR^5$, —S(=O)$R^5$, —S(=O)$_2R^5$, —NHS(=O)$_2R^5$, —C(=O)$R^5$, —OC(=O)$R^5$, —$CO_2R^5$, —$OCO_2R^5$, —CH($R^5$)$_2$, —N($R^5$)$_2$, —C(=O)N($R^5$)$_2$, —OC(=O)N($R^5$)$_2$, —NHC(=O)NH($R^5$), —NHC(=O)$R^5$, —NHC(=O)O$R^5$, —C(OH)($R^5$)$_2$, and —C($NH_2$)($R^5$)$_2$;

$R^3$ and $R^4$ are each independently selected from the group consisting of H or $C_1$-$C_6$ alkyl, wherein the alkyl group is optionally substituted with 0-5 $R^1$ groups;

each occurrence of $R^5$ is independently selected from the group consisting of H or $C_1$-$C_6$ alkyl, wherein the alkyl group is optionally substituted;

x is an integer from 0 to 5; and y is an integer from 0 to 5.

In one embodiment, ring A is a monocyclic heterocyclyl ring. In another embodiment, ring A is piperazinyl. In another embodiment, ring A is 4-methyl piperazinyl. In another embodiment, ring B is a monocyclic heteroaryl ring. In another embodiment, ring B is a 5- or 6-membered heterocyclyl or heteroaryl ring. In another embodiment, the heterocyclyl or heteroaryl ring has one heteroatom, wherein the heteroatom is alpha to the linkage between ring B and carbon 2. In another embodiment, ring B is furyl. In another embodiment, ring B is 5-nitrofuryl. In another embodiment, $R^3$ and $R^4$ are each hydrogen. In another embodiment, ring A has 1 to 2 ring heteroatoms. In another embodiment, ring A has 1 to 2 ring nitrogens. In another embodiment, at least one of $R^2$ is an electron withdrawing group. In another embodiment, the at least one $R^2$ is selected from the group consisting of F, Cl, Br, I, —CN, —$NO_2$, —C(=O)$R^5$, —$CO_2R^5$, —S(=O)$R^5$, and —S(=O)$_2R^5$. In another embodiment, the at least one $R^2$ group is beta to the linkage between ring B and carbon 2. In another embodiment, the bond between carbon 1 and carbon 2 is a double bond. In another embodiment, the compound of formula (I) is (E)-1-(4-methylpiperazin-1-yl)-3-(5-nitrofuran-2-yl)prop-2-en-1-one (NSC59984)

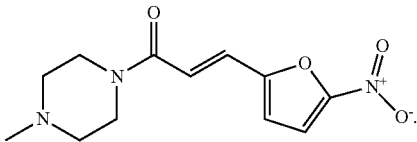

In another embodiment, the compound stimulates p73 activity, targets mutant p53 for degradation and exhibits anti-tumor effects in vivo in a p73-dependent manner.

In another embodiment, the compound exhibits anti-tumor activity against cancers associated with a p53 gain of function (GOF) mutation.

The present invention also includes a method of treating or preventing cancer in a subject. In one embodiment, the method includes administering to the subject an effective amount of the composition of the invention. In another embodiment, the cancer is associated with a p53 gain of function (GOF) mutation. In another embodiment, the cancer is selected from the group consisting of carcinomas, sarcomas, lymphomas, leukemia, blastomas, germ cell cancers, breast cancer, lung cancer, pancreatic cancer, stomach cancer, bone cancer, ovarian cancer, prostate cancer, bladder cancer, cervical cancer, colon cancer, skin cancer, gliomas, esophageal cancer, oral cancer, gallbladder cancer, liver cancer, testicular cancer, uterine cancer, thyroid cancer, and throat cancer. In another embodiment, the method further includes administering another therapy to the subject. In another embodiment, the other therapy is selected from the group consisting of radiation therapy, chemotherapy, and a combination thereof. In another embodiment, the other therapy is administered to the subject at a lower level compared to the level when administered in the absence of the compound.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIGS. 1A-1E, depicts the results of experiments demonstrating the identification of NSC59984 as a small molecule capable of restoring p53-responsive transcriptional activity in tumor cells expressing mutant p53. (FIG. 1A). Structure of NSC59984. (FIG. 1B). Imaging bioluminescence assay of p53-responsive transcriptional activity in SW480, DLD-1, HCT116 and HCT116 p53-/- cells which carry a p53-responsive luciferase reporter at 24 hr after NSC59984 treatment. Data are representative of triplicate wells. (FIG. 1C). The fold-increase of p53 responsive bioluminescence (B) in different cell lines treated with NSC59984. (FIG. 1D). mRNA levels of p21, Puma and Noxa in SW480, DLD-1, HCT116 and p53-null HCT116 cells. Cells were treated with NSC59984 for 3 hours. mRNA levels were quantified by qRT-PCR. Data were normalized to GAPDH expression and plotted relative to cells treated with DMSO as control. Data are expressed as mean±SD, *p<0.05 vs. control. (FIG. 1E). Changes of the protein levels of p53 target genes, p21, Puma, DR5 and Noxa in SW480, DLD-1, HCT116 and HCT116 p53-/- cells. Cells were treated with NSC59984 at different concentrations for 8 hr. Ran protein expression was included as a loading control.

FIGS. 2A-2G, depicts the results of experiments demonstrating that NSC59984 induces cell death in cancer cells with no genotoxicity. (FIG. 2A). Cell viability of cells treated with NSC59984 for 72 hr. Cell viability data were normalized to those of DMSO treatment as control in each cell line and data analyses were performed using PRISM4 Software (left panel). EC50 data of bioluminescence-based cell viability assay are expressed as mean±SD in normal fibroblast cells (Normal, n=3), p53 mutant cancer cells (MTp53, n=9) and cancer cells with wild-type p53 (WTp53, n=3) (right panel). (FIG. 2B). Cell cycle profiles of SW480, DLD-1, HCT116, p53-null HCT116 and normal MRC-5 and Wi38 cells at 72 hr after NSC59984 treatment. (FIG. 2C). Colony formation of cancer cells. Data represent mean±SD, *p<0.05. (FIG. 2D). Cleaved PARP protein level in cells treated with NSC59984 for 30 hr. (FIG. 2E). Genotoxicity of NSC59984 in SW480 cancer cells. SW480 cells were treated with NSC59984 at different concentrations for 8 and 16 hr. (FIG. 2F). Genotoxicity of NSC59984 in DLD-1 and HCT116 cells treated with NSC59984 for 8 hr. (FIG. 2G). SW480 cells were treated with NSC59984 and DNA damage agent etoposide (EPT) for 8 hr. Genotoxicity was measured by γH2AX.

FIGS. 3A-3C, depicts the results of experiments demonstrating the effect of NSC59984 treatment on mutant p53 and wild-type p53 protein levels. (FIG. 3A). Mutant p53 protein levels in mutant p53-expressing cancer cells treated with NSC59984. Cells were treated with different concentrations of NSC59984 for 8 hr. (FIG. 3B). Wild-type p53 protein level in MRC5 normal fibroblast cells treated with NSC59984 for 8 hr. (FIG. 3C). Wild-type p53 protein level in HCT116 cancer cells treated with NSC59984 for 8 hr. Data represent the fold-induction of p53 protein. The fold indicated is the ratio of p53:Ran as normalized to the DMSO control.

FIGS. 4A-4D, depicts the results of experiments demonstrating that NSC59984 induces mutant p53 degradation via MDM2-mediated ubiquitination. (FIG. 4A). Mutant p53 protein levels in SW480 cells treated with 10 mM MG132 and NSC59984 for 16 hr. (FIG. 4B). Mutant p53 protein levels in SW480 cells treated with 5 mM of nutlin-3 and 25 mM of NSC59984 for 16 hr. (FIG. 4C). Ubiquitination (Ub) of mutant p53 in cells treated with NSC59984 and MG132. Cells were transfected with HA-Ub for 48 hr, followed by treatment with 25 mM of NSC59984 and MG132 for 16 hr. Cell lysates were subjected to immunoprecipitation with anti p53 DO-1. Ub-mutant p53 in the immunoprecipitates was detected using the anti-HA antibody. (FIG. 4D). Mutant p53 mRNA level in SW480 cells treated with different concentrations of NSC59984. At 3 hr and 16 hr of NSC59984 treatment, mRNA was quantified by qRT-PCR. Data were normalized to GAPDH and plotted relative to cells treated with the DMSO control. Data are expressed as mean±SD.

FIGS. 5A-5C, depicts the results of experiments demonstrating that p73 is required for NSC59984 to restore the p53 pathway in mutant p53-expressing tumor cells. (FIG. 5A). NSC59984-mediated p53-responsive reporter bioluminescence in p73-overexpressing SW480 cells and in wild-type p53-overexpressing SW480 cells treated with NSC59984. SW480 cells were transfected with Ad-p73 or Ad-p53, followed by NSC59984 treatment for 8 hr. Relative bioluminescence was normalized to those of SW480 cells treated with DMSO as control. Data are expressed as mean±SD. *p<0.05. (FIG. 5B). NSC59984-mediated p53-responsive reporter bioluminescence in p73 knock-down SW480 cells. SW480 cells with stable knock-down of p73 were treated with NSC59984 at different concentrations for 8 hr. Relative bioluminescence was normalized to those of DMSO treatment. Data are expressed as mean±SD. *p<0.05. (FIG. 5C). Western blot analysis of p53 target gene expression in p73 knock-down DLD-1 cells treated with NSC59984. DLD-1 and p73-knock-down DLD-1 cells were treated with NSC59984 for 8 hr. p53 target gene protein expression was determined by Western blot.

FIGS. 6A-6E, depicts the results of experiments demonstrating that NSC59984 induces p73-dependent cell death in cancer cells. (FIG. 6A). Cell viability of p73-overexpressing DLD-1 cells treated with NSC59984. DLD-1 cells were transiently infected with Ad-p73 (stock titer was 1:1000) with double dilutions (1:2000, 1:4000, 1:8000, 1:16000, 1:32000) and followed with 1204 of NSC59984 treatment for 24 hr. Cell viability was normalized to DLD-1 cells treated with DMSO as control. Data are expressed as mean±SD. * P<0.05. (FIG. 6B). Cell viability in p73 knock-down DLD-1 and DLD-1 cells treated with NSC59984. DLD-1 and DLD-1 p73 stable knock-down cells were treated with different concentrations of NSC59984 for 72 hr. Cell viability was determined using the CellTiter-Glo assay. Cell viability was normalized to DLD-1 cells treated with DMSO as control. Data are expressed as mean±SD. *p<0.05. (FIG. 6C). Cell cycle profiles of DLD-1 and p73 knock-down DLD-1 cells after treatment with NSC59984 for 72 hr. (FIG. 6D). Cleaved PARP protein level in DLD-1 and p73 knock-down DLD-1 cells treated with NSC59984 for 24 hr. (FIG. 6E). Cell viability in SW480 cancer cells, MRC-5 and Wis38 normal fibroblast cells. Cells were treated with NSC59984 and CPT-11 for 72 hr. Cell viability in cells treated with NSC59984 and CPT11 were normalized to those treated with DMSO as control. Data are expressed as mean±SD. *p<0.05.

FIGS. 7A-7E, depicts the results of experiments demonstrating the effects of NSC59984 injection on tumor growth and cell death in xenograft tumors in vivo. Four million DLD-1 and p73 knock-down DLD-1 cells were inoculated subcutaneously into the flanks of mice. When xenograft tumors reached a size of 3-5 mm, the mice were treated with NSC59984 by i.p. injection every 5 days for two weeks. (FIG. 7A). Relative tumor volumes of the DLD-1 xenograft tumors (n=7). (FIG. 7B). Relative tumor volumes of the p73-knock-down DLD-1 xenograft tumors (n=7). (FIG. 7C). Xenograft tumor weights at day 15 after treatment (n=7). (FIG. 7D). Mouse body weights during the course of NSC59984 treatment (n=7). Data are expressed as the percent tumor growth in A and B and were normalized to tumor volume at the initiation of treatment. Tumor volumes and body weight were determined every five days. Tumor volumes were measured by caliper. Data are expressed as mean±SD. *p<0.05. (FIG. 7E). Schematic of NSC59984-mediated p53 pathway restoration via the activation of p73 and mutant p53 degradation.

FIGS. 9A-9B, depicts the results of experiments demonstrating the effect of NSC59984 treatment on the conformational change of mutant p53 in cancer cells. RXF393 and H460 cells were treated with NSC59984 for 24 hr. (FIG. 9A). Immunohistochemical staining of wild-type p53 and mutant p53 by anti-Pab1620 and anti-Pab240, respectively. H460 cells were used as a positive control for wild-type p53. (FIG. 9B). Immunoprecipitation with anti-Pab1620 was immunoblotted with anti-p53 DO-1 antibody.

DETAILED DESCRIPTION OF THE INVENTION

Figure 1:
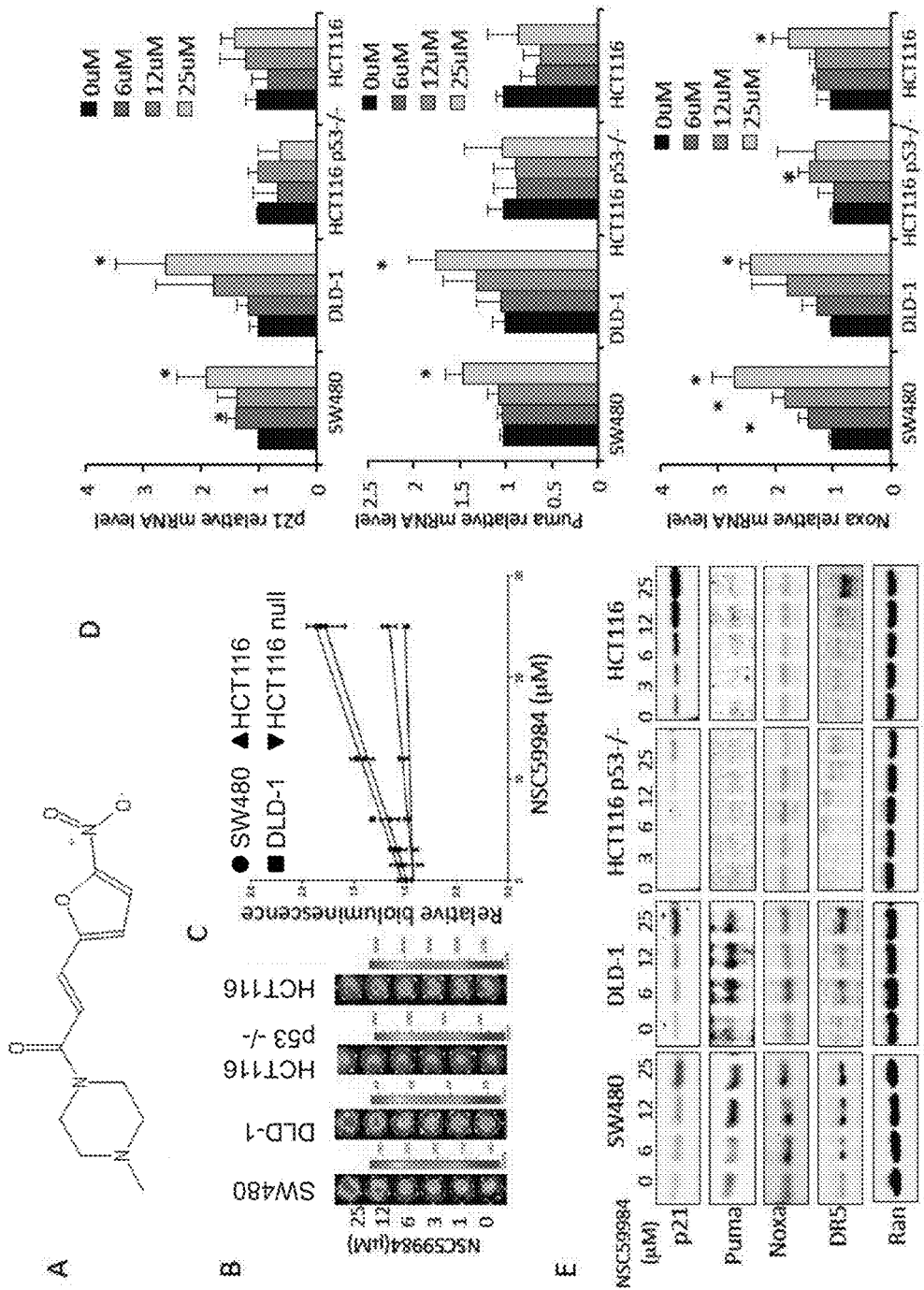
FIG. 1, comprising

This invention is based on the unexpected identification of novel compounds that have a favorable therapeutic index, is non-genotoxic at effective doses that kill tumor cells, stimulate p73 activity, target mutant p53 for degradation and display anti-tumor effects in vivo in a p73-dependent manner.

In one embodiment, the invention provides a composition and method to specifically target mutant p53 as a form of anti-cancer therapy that involves the stimulation of p73 in order to efficiently restore tumor suppression.

In one embodiment, the invention provides the use of NSC59984 [IPUAC name is (E)-1-(4-methylpiperazin-1-yl)-3-(5-nitrofuran-2yl)prop-2-en-1-one] as a lead compound for anti-cancer therapy that acts by targeting GOF mutant p53 and stimulates p73 to restore the p53 pathway signaling. Accordingly, the invention provides analogs and derivatives of NSC59984 for the use in treating cancer.

Due to their unique mechanism, the compounds contemplated within the invention are useful in overcoming the chemoresistance and radioresistance of human cancers. In one aspect, treatment of a subject with compounds contemplated within the invention enhances cell sensitivity to radiation treatments or chemotherapeutic agents, such as DNA cross-linking agents, cisplatin and mitomycin C. In another aspect, a subject treated with compounds contemplated within the invention along with a chemotherapeutic agent and/or radiation enjoys greater overall efficacy in the cancer treatment and/or prevention, as compared to the efficacy observed with the same dose of chemotherapeutic agent and/or radiation alone. In yet another aspect, a subject treated with compounds contemplated within the invention may be treated with lower doses of the chemotherapeutic agent and/or radiation of choice, and still experience similar efficacy in cancer treatment and/or prevention, as compared to the standard dose of chemotherapeutic agent and/or radiation. This has the advantage of reducing complications due to toxicity from radiation therapy or chemotherapy, and reducing recovery times for the subject.

Definitions

As used herein, each of the following terms has the meaning associated with it in this section.

Unless defined otherwise, all technical and scientific terms used herein generally have the same meaning as commonly understood by one of ordinary skill in the art to which this invention belongs. Generally, the nomenclature used herein and the laboratory procedures in biochemistry, analytical chemistry and organic chemistry are those well-known and commonly employed in the art. Standard techniques or modifications thereof are used for chemical syntheses and chemical analyses.

The articles "a" and "an" are used herein to refer to one or to more than one (i.e. to at least one) of the grammatical object of the article. By way of example, "an element" means one element or more than one element.

The term "about" will be understood by persons of ordinary skill in the art and will vary to some extent on the context in which it is used.

As used herein, the term "chemotherapeutic agent" or "chemotherapeutic agent" refers to a chemical compound, chemical conjugate, peptide, protein, antibody and the like that finds use in treating, preventing, or reducing the symptoms of cancer.

As used herein, the term "alkyl," by itself or as part of another substituent means, unless otherwise stated, a straight or branched chain hydrocarbon having the number of carbon atoms designated (i.e. $C_{1-6}$ means one to six carbon atoms) and includes straight, branched chain, or cyclic substituent groups. Examples include methyl, ethyl, propyl, isopropyl, butyl, isobutyl, tert-butyl, pentyl, neopentyl, hexyl, and cyclopropylmethyl. Most preferred is ($C_1$-$C_6$)alkyl, particularly ethyl, methyl, isopropyl, isobutyl, n-pentyl, n-hexyl and cyclopropylmethyl.

As used herein, the term "substituted alkyl" means alkyl, as defined above, substituted by one, two or three substituents selected from the group consisting of halogen, —OH, alkoxy, —NH$_2$, —N(CH$_3$)$_2$, —C(=O)OH, trifluoromethyl, —C≡N, —C(=O)O($C_1$-$C_4$)alkyl, —C(=O)NH$_2$, —SO$_2$NH$_2$, —C(=NH)NH$_2$, and —NO$_2$, preferably containing one or two substituents selected from halogen, —OH, alkoxy, —NH$_2$, trifluoromethyl, —N(CH$_3$)$_2$, and —C(=O)OH, more preferably selected from halogen, alkoxy and —OH. Examples of substituted alkyls include, but are not limited to, 2,2-difluoropropyl, 2-carboxycyclopentyl and 3-chloropropyl.

As used herein, the term "alkoxy" employed alone or in combination with other terms means, unless otherwise stated, an alkyl group having the designated number of carbon atoms, as defined above, connected to the rest of the molecule via an oxygen atom, such as, for example, methoxy, ethoxy, 1-propoxy, 2-propoxy (isopropoxy) and the higher homologs and isomers. Preferred are ($C_1$-$C_3$) alkoxy, particularly ethoxy and methoxy.

As used herein, the term "halo" or "halogen" alone or as part of another substituent means, unless otherwise stated, a fluorine, chlorine, bromine, or iodine atom, preferably, fluorine, chlorine, or bromine, more preferably, fluorine or chlorine.

As used herein, the term "heteroalkyl" by itself or in combination with another term means, unless otherwise stated, a stable straight or branched chain alkyl group consisting of the stated number of carbon atoms and one or two heteroatoms selected from the group consisting of O, N, and S, and wherein the nitrogen and sulfur atoms may be optionally oxidized and the nitrogen heteroatom may be optionally quaternized. The heteroatom(s) may be placed at any position of the heteroalkyl group, including between the rest of the heteroalkyl group and the fragment to which it is attached, as well as attached to the most distal carbon atom in the heteroalkyl group. Examples include: —O—$CH_2$—$CH_2$—$CH_3$, —$CH_2$—$CH_2$—$CH_2$—OH, —$CH_2$—$CH_2$—NH—$CH_3$, —$CH_2$—S—$CH_2$—$CH_3$, and —$CH_2CH_2$—S(=O)—$CH_3$. Up to two heteroatoms may be consecutive, such as, for example, —$CH_2$—NH—$OCH_3$, or —$CH_2$—$CH_2$—S—S—$CH_3$ As used herein, the term "aromatic" refers to a carbocycle or heterocycle with one or more polyunsaturated rings and having aromatic character, i.e. having (4n+2) delocalized π (pi) electrons, where n is an integer.

As used herein, the term "aryl," employed alone or in combination with other terms, means, unless otherwise stated, a carbocyclic aromatic system containing one or more rings (typically one, two or three rings) wherein such rings may be attached together in a pendent manner, such as a biphenyl, or may be fused, such as naphthalene. Examples include phenyl, anthracyl, and naphthyl. Preferred are phenyl and naphthyl, most preferred is phenyl.

As used herein, the term "aryl-($C_1$-$C_3$)alkyl" means a functional group wherein a one to three carbon alkylene chain is attached to an aryl group, e.g., —$CH_2CH_2$-phenyl. Preferred is aryl-$CH_2$— and aryl-CH($CH_3$)—. The term "substituted aryl-($C_1$-$C_3$)alkyl" means an aryl-($C_1$-$C_3$)alkyl functional group in which the aryl group is substituted. Preferred is substituted aryl($CH_2$)—. Similarly, the term "heteroaryl-($C_1$-$C_3$)alkyl" means a functional group wherein a one to three carbon alkylene chain is attached to a heteroaryl group, e.g., —$CH_2CH_2$-pyridyl. Preferred is heteroaryl-($CH_2$)—. The term "substituted heteroaryl-($C_1$-$C_3$) alkyl" means a heteroaryl-($C_1$-$C_3$)alkyl functional group in which the heteroaryl group is substituted. Preferred is substituted heteroaryl-($CH_2$)—.

As used herein, the term "heterocycle" or "heterocyclyl" or "heterocyclic" by itself or as part of another substituent means, unless otherwise stated, an unsubstituted or substituted, stable, mono- or multi-cyclic heterocyclic ring system that consists of carbon atoms and at least one heteroatom selected from the group consisting of N, O, and S, and wherein the nitrogen and sulfur heteroatoms may be optionally oxidized, and the nitrogen atom may be optionally quaternized. The heterocyclic system may be attached, unless otherwise stated, at any heteroatom or carbon atom that affords a stable structure. A heterocycle may be aromatic or non-aromatic in nature. In one embodiment, the heterocycle is a heteroaryl.

As used herein, the term "heteroaryl" or "heteroaromatic" refers to a heterocycle having aromatic character. A polycyclic heteroaryl may include one or more rings that are partially saturated. Examples include tetrahydroquinoline and 2,3-dihydrobenzofuryl.

Examples of non-aromatic heterocycles include monocyclic groups such as aziridine, oxirane, thiirane, azetidine, oxetane, thietane, pyrrolidine, pyrroline, imidazoline, pyrazolidine, dioxolane, sulfolane, 2,3-dihydrofuran, 2,5-dihydrofuran, tetrahydrofuran, thiophane, piperidine, 1,2,3,6-tetrahydropyridine, 1,4-dihydropyridine, piperazine, morpholine, thiomorpholine, pyran, 2,3-dihydropyran, tetrahydropyran, 1,4-dioxane, 1,3-dioxane, homopiperazine, homopiperidine, 1,3-dioxepane, 4,7-dihydro-1,3-dioxepin and hexamethyleneoxide.

Examples of heteroaryl groups include pyridyl, pyrazinyl, pyrimidinyl (particularly 2- and 4-pyrimidinyl), pyridazinyl, thienyl, furyl, pyrrolyl (particularly 2-pyrrolyl), imidazolyl, thiazolyl, oxazolyl, pyrazolyl (particularly 3- and 5-pyrazolyl), isothiazolyl, 1,2,3-triazolyl, 1,2,4-triazolyl, 1,3,4-triazolyl, tetrazolyl, 1,2,3-thiadiazolyl, 1,2,3-oxadiazolyl, 1,3,4-thiadiazolyl and 1,3,4-oxadiazolyl.

Examples of polycyclic heterocycles include indolyl (particularly 3-, 4-, 5-, 6- and 7-indolyl), indolinyl, quinolyl, tetrahydroquinolyl, isoquinolyl (particularly 1- and 5-isoquinolyl), 1,2,3,4-tetrahydroisoquinolyl, cinnolinyl, quinoxalinyl (particularly 2- and 5-quinoxalinyl), quinazolinyl, phthalazinyl, 1,8-naphthyridinyl, 1,4-benzodioxanyl, coumarin, dihydrocoumarin, 1,5-naphthyridinyl, benzofuryl (particularly 3-, 4-, 5-, 6- and 7-benzofuryl), 2,3-dihydrobenzofuryl, 1,2-benzisoxazolyl, benzothienyl (particularly 3-, 4-, 5-, 6-, and 7-benzothienyl), benzoxazolyl, benzothiazolyl (particularly 2-benzothiazolyl and 5-benzothiazolyl), purinyl, benzimidazolyl (particularly 2-benzimidazolyl), benztriazolyl, thioxanthinyl, carbazolyl, carbolinyl, acridinyl, pyrrolizidinyl, and quinolizidinyl.

The aforementioned listing of heterocyclyl and heteroaryl moieties is intended to be representative and not limiting.

As used herein, the term "substituted" means that an atom or group of atoms has replaced hydrogen as the substituent attached to another group.

As used herein, the term "optionally substituted" means that the referenced group may be substituted or unsubstituted. In one embodiment, the referenced group is optionally substituted with zero substituents, i.e., the referenced group is unsubstituted. In another embodiment, the referenced group is optionally substituted with one or more additional group(s) individually and independently selected from groups described herein.

For aryl, aryl-($C_1$-$C_3$)alkyl and heterocyclyl groups, the term "substituted" as applied to the rings of these groups refers to any level of substitution, namely mono-, di-, tri-, tetra-, or penta-substitution, where such substitution is permitted. The substituents are independently selected, and substitution may be at any chemically accessible position. In one embodiment, the substituents vary in number between one and four. In another embodiment, the substituents vary in number between one and three. In yet another embodiment, the substituents vary in number between one and two. In yet another embodiment, the substituents are independently selected from the group consisting of $C_{1-6}$ alkyl, —OH, $C_{1-6}$ alkoxy, halo, amino, acetamido and nitro. In yet another embodiment, the substituents are independently selected from the group consisting of $C_{1-6}$ alkyl, $C_{1-6}$ alkoxy, halo, acetamido, and nitro. As used herein, where a substituent is an alkyl or alkoxy group, the carbon chain may be branched, straight or cyclic, with straight being preferred.

By the term "specifically binds," as used herein, is meant a molecule, such as an antibody or a small molecule, which recognizes and binds to another molecule or feature, but does not substantially recognize or bind other molecules or features in a sample.

The phrase "inhibit," as used herein, means to reduce a molecule, a reaction, an interaction, a gene, an mRNA, and/or a protein's expression, stability, function or activity by a measurable amount or to prevent entirely. Inhibitors are compounds that, e.g., bind to, partially or totally block stimulation, decrease, prevent, delay activation, inactivate, desensitize, or down regulate a protein, a gene, and an mRNA stability, expression, function and activity, e.g., antagonists.

"Effective amount" or "therapeutically effective amount" are used interchangeably herein, and refer to an amount of a compound, formulation, material, or composition, as described herein effective to achieve a particular biological result. Such results may include, but are not limited to, the treatment of a disease or condition as determined by any means suitable in the art.

As used herein, the term "pharmaceutical composition" refers to a mixture of at least one compound of the invention with other chemical components, such as carriers, stabilizers, diluents, dispersing agents, suspending agents, thickening agents, and/or excipients. The pharmaceutical composition facilitates administration of the compound to an organism. Multiple techniques of administering a compound exist in the art including, but not limited to, intravenous, oral, aerosol, parenteral, ophthalmic, pulmonary and topical administration.

"Pharmaceutically acceptable" refers to those properties and/or substances which are acceptable to the patient from a pharmacological/toxicological point of view and to the manufacturing pharmaceutical chemist from a physical/chemical point of view regarding composition, formulation, stability, patient acceptance and bioavailability. "Pharmaceutically acceptable carrier" refers to a medium that does not interfere with the effectiveness of the biological activity of the active ingredient(s) and is not toxic to the host to which it is administered.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations. As used herein, "pharmaceutically acceptable carrier" also includes any and all coatings, antibacterial and antifungal agents, and absorption delaying agents, and the like that are compatible with the activity of the compound useful within the invention, and are physiologically acceptable to the patient. Supplementary active compounds may also be incorporated into the compositions. The "pharmaceutically acceptable carrier" may further include a pharmaceutically acceptable salt of the compound useful within the invention. Other additional ingredients that may be included in the pharmaceutical compositions used in the practice of the invention are known in the art and described, for example in Remington's Pharmaceutical Sciences (Genaro, Ed., Mack Publishing Co., 1985, Easton, Pa.), which is incorporated herein by reference.

As used herein, the term "salt" embraces addition salts of free acids or free bases that are compounds useful within the invention. Suitable acid addition salts may be prepared from an inorganic acid or from an organic acid. Examples of inorganic acids include hydrochloric, hydrobromic, hydriodic, nitric, carbonic, sulfuric, phosphoric acids, perchloric and tetrafluoroboronic acids. Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, β-hydroxybutyric, salicylic, galactaric and galacturonic acid. Suitable base addition salts of compounds useful within the invention include, for example, metallic salts including alkali metal, alkaline earth metal and transition metal salts such as, for example, lithium, calcium, magnesium, potassium, sodium and zinc salts. Acceptable base addition salts also include organic salts made from basic amines such as, for example, N,N'-dibenzylethylenediamine, chloroprocaine, choline, diethanolamine, ethylenediamine, meglumine (N-methylglucamine) and procaine. All of these salts may be prepared by conventional means from the corresponding free base compound by reacting, for example, the appropriate acid or base with the corresponding free base.

An "individual", "patient" or "subject", as that term is used herein, includes a member of any animal species including, but are not limited to, birds, humans and other primates, and other mammals including commercially relevant mammals such as cattle, pigs, horses, sheep, cats, and dogs. Preferably, the subject is a human.

The term "treat" or "treating", as used herein, means reducing the frequency with which symptoms are experienced by a subject or administering an agent or compound to reduce the frequency and/or severity with which symptoms are experienced. As used herein, "alleviate" is used interchangeably with the term "treat." Treating a disease, disorder or condition may or may not include complete eradication or elimination of the symptom.

As used herein, the term "container" includes any receptacle for holding the pharmaceutical composition. For example, in one embodiment, the container is the packaging that contains the pharmaceutical composition. In other embodiments, the container is not the packaging that contains the pharmaceutical composition, i.e., the container is a receptacle, such as a box or vial that contains the packaged pharmaceutical composition or unpackaged pharmaceutical composition and the instructions for use of the pharmaceutical composition. Moreover, packaging techniques are well known in the art. It should be understood that the instructions for use of the pharmaceutical composition may be contained on the packaging containing the pharmaceutical composition, and as such the instructions form an increased functional relationship to the packaged product. However, it should be understood that the instructions may contain information pertaining to the compound's ability to perform its intended function, e.g., treating or preventing a disease in a subject.

"Instructional material," as that term is used herein, includes a publication, a recording, a diagram, or any other medium of expression which can be used to communicate the usefulness of the composition and/or compound of the invention in a kit. The instructional material of the kit may, for example, be affixed to a container that contains the compound and/or composition of the invention or be shipped together with a container which contains the compound and/or composition. Alternatively, the instructional material may be shipped separately from the container with the intention that the recipient uses the instructional material and the compound cooperatively. Delivery of the instructional material may be, for example, by physical delivery of the publication or other medium of expression communicating the usefulness of the kit, or may alternatively be achieved by electronic transmission, for example by means of a computer, such as by electronic mail, or download from a website.

Throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

The invention provides NSC59984 as a lead compound for anti-cancer therapy that acts by targeting gain of function (GOF) mutant p53 and stimulates p73 to restore the p53 pathway signaling. NSC59984 offers a rational bypass mechanism of p53 restoration via the activation of p73 to kill cancer cells. NSC59984-mediated p53 restoration and/or activation of p73 together with depletion of p53 GOF mutant results in tumor suppression.

The invention includes compositions and methods for the treatment of a p53 related disorder. As used herein, the term "p53 related disorder" refers to any disease, disorder, or condition which is caused or characterized by activity of p53. In certain embodiments, the method of the invention is used to treat any disease, disorder or condition which is caused or characterized by the activity of p53 gain of function (GOF) mutations. In certain instances p53 GOF mutations results in the tumor growth promoting activity of p53 in addition to, or instead of, the inhibition of the normal tumor suppressive activity of p53 that may occur in certain p53 mutations. In one embodiment, the invention includes methods for the treatment of cancer. In another embodiment, the invention includes methods for the prevention of cancer.

As discussed elsewhere herein, a wide variety of cancers are, at least in part associated with p53 GOF tumor promoting activity, which leads to perpetual tumor cell growth and tumor formation. In some instances, certain p53 GOF mutations results in the enhancement of epigenetic pathways, including enhancing the expression and activity of histone modifying enzymes.

In certain embodiments, the method of the invention is used to treat any cancer associated with p53 GOF. The method is not limited to a particular type of cancer. Exemplary forms of cancer that is treatable by the method of the present invention include, but is not limited to, carcinomas, sarcomas, lymphomas, leukemia, blastomas, and germ cell cancers. For example, the methods of the invention are useful for treating or preventing breast cancer, lung cancer, pancreatic cancer, stomach cancer, bone cancer, ovarian cancer, prostate cancer, bladder cancer, cervical cancer, colon cancer, skin cancer, gliomas, esophageal cancer, oral cancer, gallbladder cancer, liver cancer, testicular cancer, uterine cancer, thyroid cancer, throat cancer, and the like.

The method of the invention may be used to treat or prevent cancer in any subject. In one embodiment, the subject is a mammal, including, but not limited to, a human, primate, cow, horse, sheep, goat, dog, cat, rodent, and the like.

Compounds Useful Within the Invention

In various embodiments, the compound is a small molecule. When the compound is a small molecule, a small molecule may be obtained using standard methods known to the skilled artisan. Such methods include chemical organic synthesis or biological means. Biological means include purification from a biological source, recombinant synthesis and in vitro translation systems, using methods well known in the art. In one embodiment, a small molecule compound of the invention comprises an organic molecule, inorganic molecule, biomolecule, synthetic molecule, and the like.

Combinatorial libraries of molecularly diverse chemical compounds potentially useful in treating a variety of diseases and conditions are well known in the art as are method of making the libraries. The method may use a variety of techniques well-known to the skilled artisan including solid phase synthesis, solution methods, parallel synthesis of single compounds, synthesis of chemical mixtures, rigid core structures, flexible linear sequences, deconvolution strategies, tagging techniques, and generating unbiased molecular landscapes for lead discovery vs. biased structures for lead development.

In a general method for small library synthesis, an activated core molecule is condensed with a number of building blocks, resulting in a combinatorial library of covalently linked, core-building block ensembles. The shape and rigidity of the core determines the orientation of the building blocks in shape space. The libraries can be biased by changing the core, linkage, or building blocks to target a characterized biological structure ("focused libraries") or synthesized with less structural bias using flexible cores.

In one embodiment, the compound of the invention is a compound of formula (I), or a salt, solvate, or N-oxide thereof:

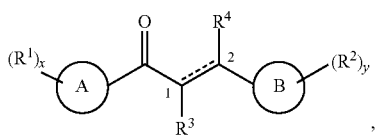

(I)

wherein in formula (I):
ring A is a monocyclic or bicyclic aryl, a monocyclic or bicyclic heteroaryl, or a monocyclic or bicyclic heterocyclyl ring, and wherein the aryl, heteroaryl, or heterocyclyl ring is optionally substituted with 0-5 $R^1$ groups;

ring B is a monocyclic or bicyclic aryl, a monocyclic or bicyclic heteroaryl, or a monocyclic or bicyclic heterocyclyl ring, and wherein the aryl, heteroaryl, or heterocyclyl ring is optionally substituted with 0-5 $R^2$ groups;

the bond between carbon 1 and carbon 2 is either a single bond or a double bond;

each occurrence of $R^1$ and $R^2$ are independently selected from the group consisting of —$C_1$-$C_6$ alkyl, —$C_1$-$C_6$ fluoroalkyl, —$C_1$-$C_6$ heteroalkyl, F, Cl, Br, I, —CN, —$NO_2$, —$OR^5$, —$SR^5$, —S(=O)$R^5$, —S(=O)$_2R^5$, —NHS(=O)$_2R^5$, —C(=O)$R^5$, —OC(=O)$R^5$, —$CO_2R^5$, —$OCO_2R^5$, —CH($R^5$)$_2$, —N($R^5$)$_2$, —C(=O)N($R^5$)$_2$, —OC(=O)N($R^5$)$_2$, —NHC(=O)NH($R^5$), —NHC(=O)$R^5$, —NHC(=O)O$R^5$, —C(OH)($R^5$)$_2$, and —C($NH_2$)($R^5$)$_2$;

$R^3$ and $R^4$ are each independently selected from the group consisting of H or $C_1$-$C_6$ alkyl, wherein the alkyl group is optionally substituted with 0-5 $R^1$ groups;

each occurrence of $R^5$ is independently selected from the group consisting of H or $C_1$-$C_6$ alkyl, wherein the alkyl group is optionally substituted;

x is an integer from 0 to 5; and
y is an integer from 0 to 5.

In one embodiment, ring A is a monocyclic heterocyclyl ring.

In one embodiment, ring A is a 5- or 6-membered heterocyclyl ring.

In one embodiment, ring A has 1 to 2 ring heteroatoms.
In one embodiment, ring A has 1 to 2 ring nitrogens.
In one embodiment, ring A is piperazinyl.
In one embodiment, ring A is 4-methyl piperazinyl.
In one embodiment, ring B is a monocyclic heteroaryl ring.

In one embodiment, ring B is furyl.
In one embodiment, ring B is 5-nitrofuryl.
In one embodiment, at least one of $R^2$ is an electron withdrawing group. Exemplary electron-withdrawing groups include halogen atoms, halogenated hydrocarbon groups such as a trifluoromethyl group, a carboxyl group, an alkoxycarbonyl group such as a methoxycarbonyl group, an aryloxycarbonyl group such as a phenoxycarbonyl group, an acyl groups such as an acetyl group, an acyloxy group such as an acetoxy group, a cyano group, an aryl group, 1-alkenyl groups, a nitro group, a sulfo group, an alkanesulfonyl group, an alkanesulfinyl group, and an alkoxysulfonyl group. In one embodiment, the electron withdrawing group is selected from the group consisting of F, Cl, Br, I, —CN, —$NO_2$, —C(=O)$R^5$, —$CO_2R^5$, —S(=O)$R^5$, and —S(=O)$_2R^5$.

In one embodiment, $R^2$ is alpha to the linkage between ring B and carbon 2. In another embodiment, $R^2$ is beta to the linkage between ring B and carbon 2.

In one embodiment, ring B contains at least one $R^2$ group, and the at least one $R^2$ is selected from the group consisting of F, Cl, Br, I, —CN, —$NO_2$, —C(=O)$R^5$, —$CO_2R^5$, —S(=O)$R^5$, and —S(=O)$_2R^5$.

In one embodiment, ring B contains at least one $R^2$ group, wherein the at least one $R^2$ is selected from the group consisting of F, Cl, Br, I, —CN, —$NO_2$, —C(=O)$R^5$, —$CO_2R^5$, —S(=O)$R^5$, and —S(=O)$_2R^5$, and the at least one $R^2$ group is beta to the linkage between ring B and carbon 2.

In one embodiment, ring B is a 5- or 6-membered heterocyclyl or heteroaryl ring. In another embodiment, the heterocyclyl or heteroaryl ring has one heteroatom, wherein the heteroatom is alpha to the linkage between ring B and carbon 2.

In one embodiment, ring B is a 5- or 6-membered heterocyclyl or heteroaryl ring, wherein the heterocyclyl or heteroaryl ring has at least one heteroatom, wherein the at least one heteroatom is alpha to the linkage between ring B and carbon 2.

In one embodiment, ring B is a 5- or 6-membered heteroaryl ring.

In one embodiment, the bond between carbon 1 and carbon 2 is a double bond.

In one embodiment, $R^3$ and $R^4$ are each hydrogen.
In one embodiment, the compound of formula (I) is (E)-1-(4-methylpiperazin-1-yl)-3-(5-nitrofuran-2-yl)prop-2-en-1-one (NSC59984)

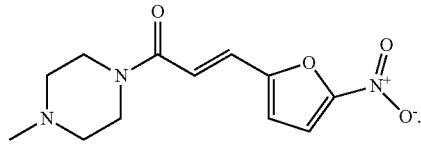

In one embodiment, the small molecule compound targets mutant p53 by stimulating p73. For example, in one embodiment, the small molecule compound which targets mutant p53 by stimulating p73 is NSC59984, or a derivative or analogue thereof.

The small molecule and small molecule compounds described herein may be present as salts even if salts are not depicted and it is understood that the invention embraces all salts and solvates of the compounds depicted here, as well as the non-salt and non-solvate form of the compounds, as is well understood by the skilled artisan. In some embodiments, the salts of the compounds of the invention are pharmaceutically acceptable salts.

Where tautomeric forms may be present for any of the compounds described herein, each and every tautomeric form is intended to be included in the present invention, even though only one or some of the tautomeric forms may be explicitly depicted. For example, when a 2-hydroxypyridyl moiety is depicted, the corresponding 2-pyridone tautomer is also intended.

The invention also includes any or all of the stereochemical forms, including any enantiomeric or diasteriomeric forms of the compounds described. The recitation of the structure or name herein is intended to embrace all possible stereoisomers of compounds depicted. All forms of the compounds are also embraced by the invention, such as crystalline or non-crystalline forms of the compounds. Compositions comprising a compound of the invention are also intended, such as a composition of substantially pure compound, including a specific stereochemical form thereof, or a composition comprising mixtures of compounds of the invention in any ratio, including two or more stereochemical forms, such as in a racemic or non-racemic mixture.

In one embodiment, the small molecule compound of the invention comprises an analog or derivative of a compound described herein.

In one embodiment, the small molecules described herein are candidates for derivatization. As such, in certain instances, the analogs of the small molecules described herein that have modulated potency, selectivity, and solubility are included herein and provide useful leads for drug discovery and drug development. Thus, in certain instances, during optimization new analogs are designed considering issues of drug delivery, metabolism, novelty, and safety.

In some instances, small molecule inhibitors described herein are derivatized/analogued as is well known in the art of combinatorial and medicinal chemistry. The analogs or derivatives can be prepared by adding and/or substituting functional groups at various locations. As such, the small molecules described herein can be converted into derivatives/analogs using well known chemical synthesis procedures. For example, all of the hydrogen atoms or substituents can be selectively modified to generate new analogs. Also, the linking atoms or groups can be modified into longer or shorter linkers with carbon backbones or hetero atoms. Also, the ring groups can be changed so as to have a different number of atoms in the ring and/or to include hetero atoms. Moreover, aromatics can be converted to cyclic rings, and vice versa. For example, the rings may be from 5-7 atoms, and may be homocycles or heterocycles.

As used herein, the term "analog," "analogue," or "derivative" is meant to refer to a chemical compound or molecule made from a parent compound or molecule by one or more chemical reactions. As such, an analog can be a structure having a structure similar to that of the small molecule compounds described herein or can be based on a scaffold of a small molecule compound described herein, but differing from it in respect to certain components or structural makeup, which may have a similar or opposite action metabolically. An analog or derivative of any of a small molecule compound in accordance with the present invention can be used to reduce skin pigmentation.

In one embodiment, the small molecule compounds described herein can independently be derivatized/analogued by modifying hydrogen groups independently from each other into other substituents. That is, each atom on each molecule can be independently modified with respect to the other atoms on the same molecule. Any traditional modification for producing a derivative/analog can be used. For example, the atoms and substituents can be independently comprised of hydrogen, an alkyl, aliphatic, straight chain aliphatic, aliphatic having a chain hetero atom, branched aliphatic, substituted aliphatic, cyclic aliphatic, heterocyclic aliphatic having one or more hetero atoms, aromatic, heteroaromatic, polyaromatic, polyamino acids, peptides, polypeptides, combinations thereof, halogens, halo-substituted aliphatics, and the like. Additionally, any ring group on a compound can be derivatized to increase and/or decrease ring size as well as change the backbone atoms to carbon atoms or hetero atoms.

Preparation of the Compounds of the Invention

Compounds of Formula (I) may be prepared using the synthetic methods known by those skilled in the art. The following examples illustrate non-limiting embodiments of the invention.

The compounds of the invention may possess one or more stereocenters, and each stereocenter may exist independently in either the R or S configuration. In one embodiment, compounds described herein are present in optically active or racemic forms. It is to be understood that the compounds described herein encompass racemic, optically-active, regioisomeric and stereoisomeric forms, or combinations thereof that possess the therapeutically useful properties described herein. Preparation of optically active forms is achieved in any suitable manner, including by way of non-limiting example, by resolution of the racemic form with recrystallization techniques, synthesis from optically-active starting materials, chiral synthesis, or chromatographic separation using a chiral stationary phase. In one embodiment, a mixture of one or more isomer is utilized as the therapeutic compound described herein. In another embodiment, compounds described herein contain one or more chiral centers. These compounds are prepared by any means, including stereoselective synthesis, enantioselective synthesis and/or separation of a mixture of enantiomers and/or diastereomers. Resolution of compounds and isomers thereof is achieved by any means including, by way of non-limiting example, chemical processes, enzymatic processes, fractional crystallization, distillation, and chromatography.

The methods and formulations described herein include the use of N-oxides (if appropriate), crystalline forms (also known as polymorphs), solvates, amorphous phases, and/or pharmaceutically acceptable salts of compounds having the structure of any compound of the invention, as well as metabolites and active metabolites of these compounds having the same type of activity. Solvates include water, ether (e.g., tetrahydrofuran, methyl tert-butyl ether) or alcohol (e.g., ethanol) solvates, acetates and the like. In one embodiment, the compounds described herein exist in solvated forms with pharmaceutically acceptable solvents such as water, and ethanol. In another embodiment, the compounds described herein exist in unsolvated form.

In one embodiment, the compounds of the invention may exist as tautomers. All tautomers are included within the scope of the compounds presented herein.

In one embodiment, compounds described herein are prepared as prodrugs. A "prodrug" refers to an agent that is converted into the parent drug in vivo.

In one embodiment, upon in vivo administration, a prodrug is chemically converted to the biologically, pharmaceutically or therapeutically active form of the compound. In another embodiment, a prodrug is enzymatically metabolized by one or more steps or processes to the biologically, pharmaceutically or therapeutically active form of the compound.

In one embodiment, sites on, for example, the aromatic ring portion of compounds of the invention are susceptible to various metabolic reactions. Incorporation of appropriate substituents on the aromatic ring structures may reduce, minimize or eliminate this metabolic pathway. In one embodiment, the appropriate substituent to decrease or eliminate the susceptibility of the aromatic ring to metabolic reactions is, by way of example only, a deuterium, a halogen, or an alkyl group.

Compounds described herein also include isotopically-labeled compounds wherein one or more atoms is replaced by an atom having the same atomic number, but an atomic mass or mass number different from the atomic mass or mass number usually found in nature. Examples of isotopes suitable for inclusion in the compounds described herein include and are not limited to $^{2}H$, $^{3}H$, $^{11}C$, $^{13}C$, $^{14}C$, $^{36}Cl$, $^{18}F$, $^{123}I$, $^{125}I$, $^{13}N$, $^{15}N$, $^{15}O$, $^{17}O$, $^{18}O$, $^{32}P$, and $^{35}S$. In one embodiment, isotopically-labeled compounds are useful in drug and/or substrate tissue distribution studies. In another embodiment, substitution with heavier isotopes such as deuterium affords greater metabolic stability (for example, increased in vivo half-life or reduced dosage requirements). In yet another embodiment, substitution with positron emitting isotopes, such as $^{11}$C, $^{18}$F, 15O and $^{13}$N, is useful in Positron Emission Topography (PET) studies for examining substrate receptor occupancy. Isotopically-labeled compounds are prepared by any suitable method or by processes using an appropriate isotopically-labeled reagent in place of the non-labeled reagent otherwise employed.

In one embodiment, the compounds described herein are labeled by other means, including, but not limited to, the use of chromophores or fluorescent moieties, bioluminescent labels, or chemiluminescent labels.

The compounds described herein, and other related compounds having different substituents are synthesized using techniques and materials described herein and as described, for example, in Fieser & Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), Larock's Comprehensive Organic Transformations (VCH Publishers Inc., 1989), March, Advanced Organic Chemistry 4$^{th}$ Ed., (Wiley 1992); Carey & Sundberg, Advanced Organic Chemistry 4th Ed., Vols. A and B (Plenum 2000, 2001), and Green & Wuts, Protective Groups in Organic Synthesis 3rd Ed., (Wiley 1999) (all of which are incorporated by reference for such disclosure). General methods for the preparation of compound as described herein are modified by the use of appropriate reagents and conditions, for the introduction of the various moieties found in the formula as provided herein.

Compounds described herein are synthesized using any suitable procedures starting from compounds that are available from commercial sources, or are prepared using procedures described herein.

In one embodiment, reactive functional groups, such as hydroxyl, amino, imino, thio or carboxy groups, are protected in order to avoid their unwanted participation in reactions. Protecting groups are used to block some or all of the reactive moieties and prevent such groups from participating in chemical reactions until the protective group is removed. In another embodiment, each protective group is removable by a different means. Protective groups that are cleaved under totally disparate reaction conditions fulfill the requirement of differential removal.

In one embodiment, protective groups are removed by acid, base, reducing conditions (such as, for example, hydrogenolysis), and/or oxidative conditions. Groups such as trityl, dimethoxytrityl, acetal and t-butyldimethylsilyl are acid labile and are used to protect carboxy and hydroxy reactive moieties in the presence of amino groups protected with Cbz groups, which are removable by hydrogenolysis, and Fmoc groups, which are base labile. Carboxylic acid and hydroxy reactive moieties are blocked with base labile groups such as, but not limited to, methyl, ethyl, and acetyl, in the presence of amines that are blocked with acid labile groups, such as t-butyl carbamate, or with carbamates that are both acid and base stable but hydrolytically removable.

In one embodiment, carboxylic acid and hydroxy reactive moieties are blocked with hydrolytically removable protective groups such as the benzyl group, while amine groups capable of hydrogen bonding with acids are blocked with base labile groups such as Fmoc. Carboxylic acid reactive moieties are protected by conversion to simple ester compounds as exemplified herein, which include conversion to alkyl esters, or are blocked with oxidatively-removable protective groups such as 2,4-dimethoxybenzyl, while co-existing amino groups are blocked with fluoride labile silyl carbamates.

Allyl blocking groups are useful in the presence of acid- and base-protecting groups since the former are stable and are subsequently removed by metal or pi-acid catalysts. For example, an allyl-blocked carboxylic acid is deprotected with a palladium-catalyzed reaction in the presence of acid labile t-butyl carbamate or base-labile acetate amine protecting groups. Yet another form of protecting group is a resin to which a compound or intermediate is attached. As long as the residue is attached to the resin, that functional group is blocked and does not react. Once released from the resin, the functional group is available to react.

Typically blocking/protecting groups may be selected from:

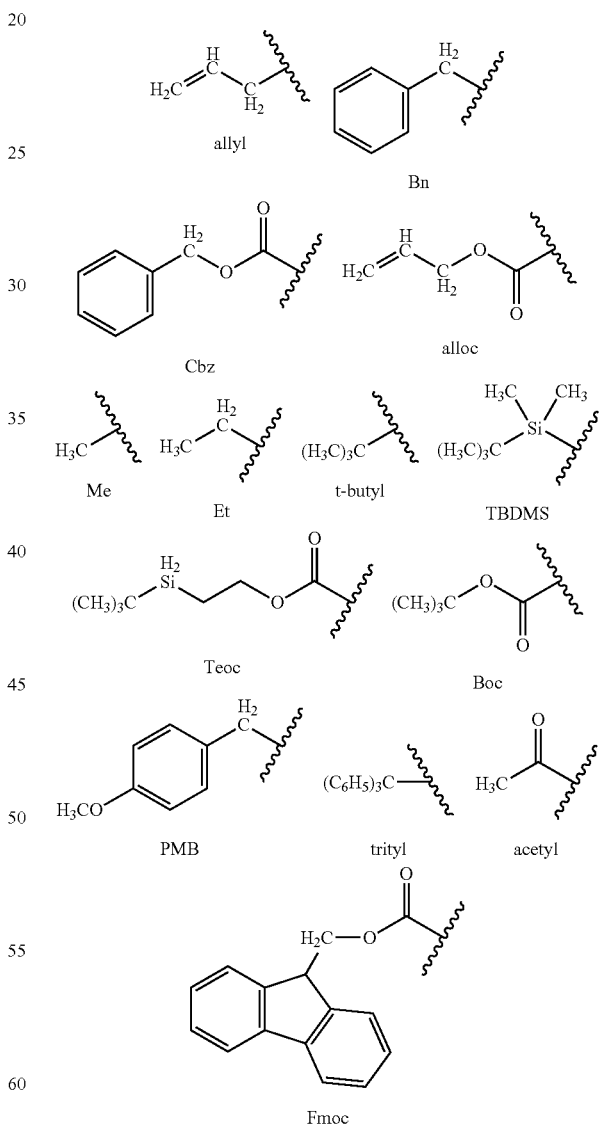

Other protecting groups, plus a detailed description of techniques applicable to the creation of protecting groups and their removal are described in Greene & Wuts, Protective Groups in Organic Synthesis, 3rd Ed., John Wiley &

Sons, New York, N.Y., 1999, and Kocienski, Protective Groups, Thieme Verlag, New York, N.Y., 1994, which are incorporated herein by reference for such disclosure.

Salts

The compounds described herein may form salts with acids, and such salts are included in the present invention. In one embodiment, the salts are pharmaceutically acceptable salts. The term "salts" embraces addition salts of free acids or bases that are useful within the methods of the invention. The term "pharmaceutically acceptable salt" refers to salts that possess toxicity profiles within a range that affords utility in pharmaceutical applications. Pharmaceutically unacceptable salts may nonetheless possess properties such as high crystallinity, which have utility in the practice of the present invention, such as for example utility in process of synthesis, purification or formulation of compounds useful within the methods of the invention.

Suitable pharmaceutically acceptable acid addition salts may be prepared from an inorganic acid or from an organic acid. Examples of inorganic acids include sulfate, hydrogen sulfate, hydrochloric, hydrobromic, hydriodic, nitric, carbonic, sulfuric, and phosphoric acids (including hydrogen phosphate and dihydrogen phosphate). Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, β-hydroxybutyric, salicylic, galactaric and galacturonic acid.

Suitable pharmaceutically acceptable base addition salts of compounds of the invention include, for example, metallic salts including alkali metal, alkaline earth metal and transition metal salts such as, for example, calcium, magnesium, potassium, sodium and zinc salts. Pharmaceutically acceptable base addition salts also include organic salts made from basic amines such as, for example, N,N'-dibenzylethylene-diamine, chloroprocaine, choline, diethanolamine, ethylenediamine, meglumine (N-methylglucamine) and procaine.

All of these salts may be prepared from the corresponding compound by reacting, for example, the appropriate acid or base with the compound.

Combination Therapies

The compounds contemplated within the invention or salts thereof may be useful in the methods of present invention in combination with radiation therapy and/or a compound useful for treating cancer (generally referred to as "chemotherapeutic agent"). These additional compounds may comprise compounds of the present invention or compounds (such as commercially available compounds) known to treat, prevent, or reduce the symptoms of cancer. In one embodiment, the combination of a compound contemplated within the invention and a chemotherapeutic agent has additive, complementary or synergistic effects in the treatment of cancer in a subject, or prevention of cancer in a subject. In another embodiment, the combination of a compound contemplated within the invention and radiation therapy has additive, complementary or synergistic effects in the treatment of cancer in a subject, or prevention of cancer in a subject.

Radiation Therapy

In one aspect, a compound contemplated within the invention or a salt thereof may be used in combination with radiation therapy.

Radiation therapy, radiation oncology, or radiotherapy, sometimes abbreviated to XRT, is the medical use of ionizing radiation as part of cancer treatment to control malignant cells. Radiotherapy may be used for curative or adjuvant treatment. It is used as palliative treatment (where cure is not possible and the aim is for local disease control or symptomatic relief) or as therapeutic treatment (where the therapy has survival benefit and it can be curative).

Radiotherapy is used for the treatment of malignant cancer, and may be used as a primary or adjuvant modality. It is also common to combine radiotherapy with surgery, chemotherapy, hormone therapy, immunotherapy or a mixture of the four. Most common cancer types can be treated with radiotherapy in some way. The precise treatment intent (curative, adjuvant, neoadjuvant, therapeutic, or palliative) will depend on the tumor type, location, and stage, as well as the general health of the patient.

Radiation therapy is commonly applied to the cancerous tumor. The radiation fields may also include the draining lymph nodes if they are clinically or radiologically involved with tumor, or if there is thought to be a risk of subclinical malignant spread. Brachytherapy, in which a radiation source is placed inside or next to the area requiring treatment, is another form of radiation therapy that minimizes exposure to healthy tissue during procedures to treat cancers of the breast, prostate and other organs.

The amount of radiation used in photon radiation therapy is measured in gray (Gy), and varies depending on the type and stage of cancer being treated. For curative cases, the typical dose for a solid epithelial tumor ranges from 60 to 80 Gy, while lymphomas are treated with 20 to 40 Gy. Preventative (adjuvant) doses are typically around 45-60 Gy in 1.8-2 Gy fractions (for breast, head, and neck cancers.) Many other factors are considered by radiation oncologists when selecting a dose, including whether the patient is receiving chemotherapy, patient comorbidities, whether radiation therapy is being administered before or after surgery, and the degree of success of surgery.

Chemotherapeutic Agents

In one aspect of the invention, a compound of the invention or a salt thereof may be used in combination with a chemotherapeutic agent.

In one embodiment, a compound of the invention is co-administered with a chemotherapeutic agent to the subject in need thereof. In another embodiment, a compound of the invention and a chemotherapeutic agent are administered to the subject as part of the same pharmaceutical formulation. In yet another embodiment, a compound of the invention and a chemotherapeutic agent are administered separately to the subject in need thereof.

Most of the approved chemotherapeutic agents may be divided into alkylating agents, antimetabolites, anthracyclines, plant alkaloids and terpenoids, topoisomerase inhibitors, antineoplastics and other antitumour agents. These drugs affect cell division or DNA synthesis and function directly or indirectly.

Some newer chemotherapeutic agents do not directly interfere with DNA synthesis and function. These include monoclonal antibodies and tyrosine kinase inhibitors e.g. imatinib mesylate (Gleevec or Glivec), which directly targets a molecular abnormality in certain types of cancer (chronic myelogenous leukemia, gastrointestinal stromal tumors), and are generally referred to as targeted therapies.

In addition, some drugs that modulate tumor cell behavior without directly attacking those cells, such as hormones, may be used in the treatment of cancer.

Non-limiting examples of chemotherapeutic agents are provided below.

Alkylating Agents:

Alkylating agents alkylate nucleophilic functional groups present in cells. They impair cell function by forming covalent bonds with the amino, carboxyl, sulfhydryl, and phosphate groups in biologically important molecules, and in particular by chemically modifying a cell's DNA. Cisplatin, carboplatin, oxaliplatin, mechlorethamine, cyclophosphamide, chlorambucil, and ifosfamide are alkylating agents.

Anti-Metabolites:

Anti-metabolites masquerade as purines (azathioprine, mercaptopurine) or pyrimidines, which are building blocks of DNA. By competing out naturally occurring purines or pyrimidines, anti-metabolites prevent these building blocks from becoming incorporated into DNA during the "S" phase (of the cell cycle), thus stopping normal development and division. Anti-metabolites also affect RNA synthesis. Due to their efficiency, anti-metabolites are the most widely used cytostatics.

Plant Alkaloids and Terpenoids:

These plant alkaloids block cell division by preventing microtubule function. Microtubules are vital for cell division, and, without them, cell division cannot occur. The main examples of plant alkaloids are vinca alkaloids and taxanes.

(a) Vinca Alkaloids

Vinca alkaloids bind to specific sites on tubulin, inhibiting assembly of tubulin into microtubules (M phase of the cell cycle). The vinca alkaloids include vincristine, vinblastine, vinorelbine and vindesine.

(b) Podophyllotoxin

Podophyllotoxin is a plant-derived compound said to help with digestion and used to produce two other cytostatic drugs, etoposide and teniposide. They prevent the cell from entering the G1 phase (the start of DNA replication) and the replication of DNA (the S phase). The exact mechanism of its action is unknown. The substance has been primarily obtained from the American Mayapple (*Podophyllum peltatum*). Recently it has been discovered that a rare Himalayan Mayapple (*Podophyllum hexandrum*) contains it in a much greater quantity, but, as the plant is endangered, its supply is limited. Studies have been conducted to isolate the genes involved in the substance's production, so that it could be obtained recombinantly.

(c) Taxanes

The prototype taxane is the natural product paclitaxel, originally known as Taxol and first derived from the bark of the Pacific Yew tree. Docetaxel is a semi-synthetic analogue of paclitaxel. Taxanes enhance stability of microtubules, preventing the separation of chromosomes during anaphase.

Topoisomerase Inhibitors:

Topoisomerases are essential enzymes that maintain the topology of DNA. Inhibition of type I or type II topoisomerases interferes with both transcription and replication of DNA by upsetting proper DNA supercoiling. Type I topoisomerase inhibitors include camptothecins: irinotecan and topotecan. Type II inhibitors include amsacrine, etoposide, etoposide phosphate, and teniposide. These are semisynthetic derivatives of epipodophyllotoxins, alkaloids naturally occurring in the root of American Mayapple (*Podophyllum peltatum*).

Antineoplastics:

These include the immunosuppressant dactinomycin (which is used in kidney transplantations), doxorubicin, epirubicin, bleomycin and others.

Anticancer agents working through different cytotoxic mechanisms may also be combined in "chemotherapy regimens" in order to target a specific type of cancer. Chemotherapy regimens are often identified by acronyms, identifying the agents used in combination. However, the letters used are not consistent across regimens, and in some cases (for example, "BEACOPP"), the same letter combination is used to represent two different treatments. Non-limiting examples of combinations used in clinical settings are listed below, in terms of acronyms, compositions and cancer types:

ABVD: Adriamycin (doxorubicin), bleomycin, vinblastine, dacarbazine—Hodgkin's lymphoma AC: Adriamycin (doxorubicin), cyclophosphamide—Breast cancer BEACOPP: Bleomycin, etoposide, Adriamycin (doxorubicin), cyclophosphamide, Oncovin (vincristine), procarbazine, prednisone—Hodgkin's lymphoma BEP: Bleomycin, etoposide, platinum agent (cisplatin)—Testicular cancer, germ cell tumors CA: Cyclophosphamide, Adriamycin (doxorubicin) (same as AC)—Breast cancer CAF: Cyclophosphamide, Adriamycin (doxorubicin), fluorouracil (5-FU)—Breast cancer CAV: Cyclophosphamide, Adriamycin (doxorubicin), vincristine—Lung cancer CBV: Cyclophosphamide, BCNU (carmustine), VP-16 (etoposide)—Lymphoma Ch1VPP/EVA: Chlorambucil, vincristine (Oncovin), procarbazine, prednisone, etoposide, vinblastine, Adriamycin (doxorubicin)—Hodgkin's lymphoma CHOP: Cyclophosphamide, hydroxydoxorubicin (doxorubicin), vincristine (Oncovin), prednisone—Non-Hodgkin lymphoma CHOP-R or R-CHOP: CHOP+rituximab—B cell non-Hodgkin lymphoma COP or CVP: Cyclophosphamide, Oncovin (vincristine), prednisone—Non-Hodgkin lymphoma in patients with history of cardiovascular disease CMF: Cyclophosphamide, methotrexate, fluorouracil (5-FU)—Breast cancer COPP: Cyclophosphamide, Oncovin (vincristine), procarbazine, prednisone—Non-Hodgkin lymphoma EC: Epirubicin, cyclophosphamide—Breast cancer ECF: Epirubicin, cisplatin, fluorouracil (5-FU)—Gastric cancer and oesophageal cancer EP: Etoposide, platinum agent (cisplatin)—Testicular cancer, germ cell tumors EPOCH: Etoposide, prednisone, Oncovin, cyclophosphamide, and hydroxydaunorubicin—Lymphomas FEC: Fluorouracil (5-FU), epirubicin, cyclophosphamide—Breast cancer FL (Also known as Mayo): Fluorouracil (5-FU), leucovorin (folinic acid)—Colorectal cancer FOLFOX: Fluorouracil (5-FU), leucovorin (folinic acid), oxaliplatin—Colorectal cancer FOLFIRI: Fluorouracil (5-FU), leucovorin (folinic acid), irinotecan—Colorectal cancer ICE: ifosfamide, carboplatin, etoposide (VP-16)—Aggressive lymphomas, progressive neuroblastoma ICE-R: ICE+rituximab—High-risk progressive or recurrent lymphomas m-BACOD: Methotrexate, bleomycin, Adriamycin (doxorubicin), cyclophosphamide, Oncovin (vincristine), dexamethasone—Non-Hodgkin lymphoma MACOP-B: Methotrexate, leucovorin (folinic acid), Adriamycin (doxorubicin), cyclophosphamide, Oncovin (vincristine), prednisone, bleomycin—Non-Hodgkin lymphoma MOPP: Mechlorethamine, Oncovin (vincristine), procarbazine, prednisone—Hodgkin's lymphoma MVAC: methotrexate, vinblastine, adriamycin, cisplatin—Advanced bladder cancer[2]

PCV: Procarbazine, CCNU (lomustine), vincristine—Brain tumors

ProMACE-MOPP: Methotrexate, Adriamycin (doxorubicin), cyclophosphamide, etoposide+MOPP—Non-Hodgkin lymphoma ProMACE-CytaBOM: Prednisone, doxorubicin (adriamycin), cyclophosphamide, etoposide, cytarabine, bleomycin, Oncovin (vincristine), methotrexate, leucovorin—Non-Hodgkin lymphoma R-FCM: Rituximab, fludarabine, cyclophosphamide, mitoxantrone—B cell non-Hodgkin lymphoma Stanford V: Doxorubicin, mechlorethamine, bleomycin, vinblastine, vincristine, etoposide, prednisone—Hodgkin's lymphoma Thal/Dex: Thalidomide, dexamethasone—Multiple myeloma TIP: Paclitaxel, ifosfamide, platinum agent cisplatin—Testicular cancer, germ cell tumors in salvage therapy VAC: Vincristine, Actinomycin, Cyclophosphamide—Rhabdomyosarcoma VAD: Vincristine, Adriamycin (doxorubicin), dexamethasone—Multiple myeloma VAPEC-B: Vincristine, Adriamycin (doxorubicin), prednisone, etoposide, cyclophosphamide, bleomycin—Hodgkin's lymphoma VIP: Etoposide, ifosfamide, platinum agent cisplatin—Testicular cancer, germ cell tumors A synergistic effect may be calculated, for example, using suitable methods such as, for example, the Sigmoid-$E_{max}$ equation (Holford & Scheiner, 19981, Clin. Pharmacokinet. 6: 429-453), the equation of Loewe additivity (Loewe & Muischnek, 1926, Arch. Exp. Pathol Pharmacol. 114: 313-326) and the median-effect equation (Chou & Talalay, 1984, Adv. Enzyme Regul. 22: 27-55). Each equation referred to above may be applied to experimental data to generate a corresponding graph to aid in assessing the effects of the drug combination. The corresponding graphs associated with the equations referred to above are the concentration-effect curve, isobologram curve and combination index curve, respectively.

Pharmaceutical Compositions and Therapies

Administration of a compound useful within the invention may be achieved in a number of different ways, using methods known in the art. The therapeutic and prophylactic methods of the invention thus encompass the use of pharmaceutical compositions comprising the compounds useful within the invention to practice the methods of the invention. The pharmaceutical compositions useful for practicing the invention may be administered to deliver a dose of 1 ng/kg/day to 100 mg/kg/day.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

Although the description of pharmaceutical compositions provided herein are principally directed to pharmaceutical compositions that are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, mammals including commercially relevant mammals such as non-human primates, cattle, pigs, horses, sheep, cats, and dogs.

Typically, dosages which may be administered in a method of the invention to an animal, preferably a human, range in amount from 0.5 µg to about 50 mg per kilogram of body weight of the animal. While the precise dosage administered will vary depending upon any number of factors, including but not limited to, the type of animal and type of disease state being treated, the age of the animal and the route of administration, the dosage of the compound will preferably vary from about 1 µg to about 10 mg per kilogram of body weight of the animal. More preferably, the dosage will vary from about 3 µg to about 1 mg per kilogram of body weight of the animal.

Pharmaceutical compositions that are useful in the methods of the invention may be prepared, packaged, or sold in formulations suitable for oral, parenteral, topical, buccal, or another route of administration. Other contemplated formulations include projected nanoparticles, liposomal preparations, resealed erythrocytes containing the active ingredient, and immunologically-based formulations.

The formulations of the pharmaceutical compositions described herein may be prepared by any method known or hereafter developed in the art of pharmacology. In general, such preparatory methods include the step of bringing the active ingredient into association with a pharmaceutically acceptable carrier or one or more other accessory ingredients, and then, if necessary or desirable, shaping or packaging the product into a desired single- or multi-dose unit.

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient that would be administered to a subject or a convenient fraction of such a dosage such as, for example, one-half or one-third of such a dosage.

In one embodiment, the compositions of the invention are formulated using one or more pharmaceutically acceptable excipients or carriers. In one embodiment, the pharmaceutical compositions of the invention comprise a therapeutically effective amount of a compound or conjugate of the invention and a pharmaceutically acceptable carrier. Pharmaceutically acceptable carriers that are useful, include, but are not limited to, glycerol, water, saline, ethanol and other pharmaceutically acceptable salt solutions such as phosphates and salts of organic acids. Examples of these and other pharmaceutically acceptable carriers are described in Remington's Pharmaceutical Sciences (1991, Mack Publication Co., New Jersey).

The carrier may be a solvent or dispersion medium containing, for example, water, ethanol, polyol (for example, glycerol, propylene glycol, and liquid polyethylene glycol, and the like), suitable mixtures thereof, and vegetable oils. The proper fluidity may be maintained, for example, by the use of a coating such as lecithin, by the maintenance of the required particle size in the case of dispersion and by the use of surfactants. Prevention of the action of microorganisms may be achieved by various antibacterial and antifungal agents, for example, parabens, chlorobutanol, phenol, ascorbic acid, thimerosal, and the like. In many cases, it will be preferable to include isotonic agents, for example, sugars, sodium chloride, or polyalcohols such as mannitol and sorbitol, in the composition. Prolonged absorption of the injectable compositions may be brought about by including in the composition an agent that delays absorption, for example, aluminum monostearate or gelatin. In one embodiment, the pharmaceutically acceptable carrier is not DMSO alone.

Formulations may be employed in admixtures with conventional excipients, i.e., pharmaceutically acceptable organic or inorganic carrier substances suitable for oral, parenteral, nasal, intravenous, subcutaneous, enteral, or any other suitable mode of administration, known to the art. The pharmaceutical preparations may be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like. They may also be combined where desired with other active agents, e.g., other analgesic agents.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" that may be included in the pharmaceutical compositions of the invention are known in the art and described, for example in Genaro, ed. (1985, Remington's Pharmaceutical Sciences, Mack Publishing Co., Easton, Pa.), which is incorporated herein by reference.

The composition of the invention may comprise a preservative from about 0.005% to 2.0% by total weight of the composition. The preservative is used to prevent spoilage in the case of exposure to contaminants in the environment. Examples of preservatives useful in accordance with the invention included but are not limited to those selected from the group consisting of benzyl alcohol, sorbic acid, parabens, imidurea and combinations thereof. A particularly preferred preservative is a combination of about 0.5% to 2.0% benzyl alcohol and 0.05% to 0.5% sorbic acid.

The composition preferably includes an anti-oxidant and a chelating agent that inhibits the degradation of the compound. Preferred antioxidants for some compounds are BHT, BHA, alpha-tocopherol and ascorbic acid in the preferred range of about 0.01% to 0.3% and more preferably BHT in the range of 0.03% to 0.1% by weight by total weight of the composition. Preferably, the chelating agent is present in an amount of from 0.01% to 0.5% by weight by total weight of the composition. Particularly preferred chelating agents include edetate salts (e.g. disodium edetate) and citric acid in the weight range of about 0.01% to 0.20% and more preferably in the range of 0.02% to 0.10% by weight by total weight of the composition. The chelating agent is useful for chelating metal ions in the composition that may be detrimental to the shelf life of the formulation. While BHT and disodium edetate are the particularly preferred antioxidant and chelating agent respectively for some compounds, other suitable and equivalent antioxidants and chelating agents may be substituted therefore as would be known to those skilled in the art.

Liquid suspensions may be prepared using conventional methods to achieve suspension of the active ingredient in an aqueous or oily vehicle. Aqueous vehicles include, for example, water, and isotonic saline. Oily vehicles include, for example, almond oil, oily esters, ethyl alcohol, vegetable oils such as arachis, olive, sesame, or coconut oil, fractionated vegetable oils, and mineral oils such as liquid paraffin. Liquid suspensions may further comprise one or more additional ingredients including, but not limited to, suspending agents, dispersing or wetting agents, emulsifying agents, demulcents, preservatives, buffers, salts, flavorings, coloring agents, and sweetening agents. Oily suspensions may further comprise a thickening agent. Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, hydroxypropylmethylcellulose. Known dispersing or wetting agents include, but are not limited to, naturally-occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g., polyoxyethylene stearate, heptadecaethyleneoxycetanol, polyoxyethylene sorbitol monooleate, and polyoxyethylene sorbitan monooleate, respectively). Known emulsifying agents include, but are not limited to, lecithin, and acacia. Known preservatives include, but are not limited to, methyl, ethyl, or n-propyl-para-hydroxybenzoates, ascorbic acid, and sorbic acid. Known sweetening agents include, for example, glycerol, propylene glycol, sorbitol, sucrose, and saccharin. Known thickening agents for oily suspensions include, for example, beeswax, hard paraffin, and cetyl alcohol.

Liquid solutions of the active ingredient in aqueous or oily solvents may be prepared in substantially the same manner as liquid suspensions, the primary difference being that the active ingredient is dissolved, rather than suspended in the solvent. As used herein, an "oily" liquid is one which comprises a carbon-containing liquid molecule and which exhibits a less polar character than water. Liquid solutions of the pharmaceutical composition of the invention may comprise each of the components described with regard to liquid suspensions, it being understood that suspending agents will not necessarily aid dissolution of the active ingredient in the solvent. Aqueous solvents include, for example, water, and isotonic saline. Oily solvents include, for example, almond oil, oily esters, ethyl alcohol, vegetable oils such as arachis, olive, sesame, or coconut oil, fractionated vegetable oils, and mineral oils such as liquid paraffin.

Powdered and granular formulations of a pharmaceutical preparation of the invention may be prepared using known methods. Such formulations may be administered directly to a subject, used, for example, to form tablets, to fill capsules, or to prepare an aqueous or oily suspension or solution by addition of an aqueous or oily vehicle thereto. Each of these formulations may further comprise one or more of dispersing or wetting agent, a suspending agent, and a preservative. Additional excipients, such as fillers and sweetening, flavoring, or coloring agents, may also be included in these formulations.

A pharmaceutical composition of the invention may also be prepared, packaged, or sold in the form of oil-in-water emulsion or a water-in-oil emulsion. The oily phase may be a vegetable oil such as olive or arachis oil, a mineral oil such as liquid paraffin, or a combination of these. Such compositions may further comprise one or more emulsifying agents such as naturally occurring gums such as gum acacia or gum tragacanth, naturally-occurring phosphatides such as soybean or lecithin phosphatide, esters or partial esters derived from combinations of fatty acids and hexitol anhydrides such as sorbitan monooleate, and condensation products of such partial esters with ethylene oxide such as polyoxyethylene sorbitan monooleate. These emulsions may also contain additional ingredients including, for example, sweetening or flavoring agents.

Methods for impregnating or coating a material with a chemical composition are known in the art, and include, but are not limited to methods of depositing or binding a chemical composition onto a surface, methods of incorporating a chemical composition into the structure of a material during the synthesis of the material (i.e., such as with a physiologically degradable material), and methods of absorbing an aqueous or oily solution or suspension into an absorbent material, with or without subsequent drying.

Administration/Dosing

The regimen of administration may affect what constitutes an effective amount. The therapeutic formulations may be administered to the subject either prior to or after a diagnosis of disease. Further, several divided dosages, as well as staggered dosages may be administered daily or sequentially, or the dose may be continuously infused, or may be a bolus injection. Further, the dosages of the therapeutic formulations may be proportionally increased or decreased as indicated by the exigencies of the therapeutic or prophylactic situation.

Administration of the compositions of the present invention to a subject, preferably a mammal, more preferably a human, may be carried out using known procedures, at dosages and for periods of time effective to prevent or treat disease. An effective amount of the therapeutic compound necessary to achieve a therapeutic effect may vary according to factors such as the activity of the particular compound employed; the time of administration; the rate of excretion of the compound; the duration of the treatment; other drugs, compounds or materials used in combination with the compound; the state of the disease or disorder, age, sex, weight, condition, general health and prior medical history of the subject being treated, and like factors well-known in the medical arts. Dosage regimens may be adjusted to provide the optimum therapeutic response. For example, several divided doses may be administered daily or the dose may be proportionally reduced as indicated by the exigencies of the therapeutic situation. A non-limiting example of an effective dose range for a therapeutic compound of the invention is from about 1 and 5,000 mg/kg of body weight/per day. One of ordinary skill in the art would be able to study the relevant factors and make the determination regarding the effective amount of the therapeutic compound without undue experimentation.

The compound may be administered to an animal as frequently as several times daily, or it may be administered less frequently, such as once a day, once a week, once every two weeks, once a month, or even less frequently, such as once every several months or even once a year or less. The frequency of the dose will be readily apparent to the skilled artisan and will depend upon any number of factors, such as, but not limited to, the type and severity of the disease being treated, the type and age of the animal, etc. The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

Actual dosage levels of the active ingredients in the pharmaceutical compositions of this invention may be varied so as to obtain an amount of the active ingredient that is effective to achieve the desired therapeutic response for a particular subject, composition, and mode of administration, without being toxic to the subject.

A medical doctor, e.g., physician or veterinarian, having ordinary skill in the art may readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In particular embodiments, it is especially advantageous to formulate the compound in dosage unit form for ease of administration and uniformity of dosage. Dosage unit form as used herein refers to physically discrete units suited as unitary dosages for the subjects to be treated; each unit containing a predetermined quantity of therapeutic compound calculated to produce the desired therapeutic effect in association with the required pharmaceutical vehicle. The dosage unit forms of the invention are dictated by and directly dependent on (a) the unique characteristics of the therapeutic compound and the particular therapeutic effect to be achieved, and (b) the limitations inherent in the art of compounding/formulating such a therapeutic compound for the treatment of a disease in a subject.

In one embodiment, the compositions of the invention are administered to the subject in dosages that range from one to five times per day or more. In another embodiment, the compositions of the invention are administered to the subject in range of dosages that include, but are not limited to, once every day, every two, days, every three days to once a week, and once every two weeks. It will be readily apparent to one skilled in the art that the frequency of administration of the various combination compositions of the invention will vary from subject to subject depending on many factors including, but not limited to, age, disease or disorder to be treated, gender, overall health, and other factors. Thus, the invention should not be construed to be limited to any particular dosage regime and the precise dosage and composition to be administered to any subject will be determined by the attending physical taking all other factors about the subject into account.

Compounds of the invention for administration may be in the range of from about 0.1 mg to about 1,000 mg, about 0.2 mg to about 950 mg, about 0.4 mg to about 900 mg, about 1 mg to about 850 mg, about 5 mg to about 750 mg, about 20 mg to about 700 mg, about 30 mg to about 600 mg, about 50 mg to about 500 mg, about 75 mg to about 400 mg, about 100 mg to about 300 mg, about 120 mg to about 250 mg, and any and all whole or partial increments therebetween.

In some embodiments, the dose of a compound of the invention is from about 1 mg and about 2,500 mg. In some embodiments, a dose of a compound of the invention used in compositions described herein is less than about 10,000 mg, or less than about 8,000 mg, or less than about 6,000 mg, or less than about 5,000 mg, or less than about 3,000 mg, or less than about 2,000 mg, or less than about 1,000 mg, or less than about 500 mg, or less than about 200 mg, or less than about 50 mg. Similarly, in some embodiments, a dose of a second compound (i.e., a drug used for treating the same or another disease as that treated by the compositions of the invention) as described herein is less than about 1,000 mg, or less than about 800 mg, or less than about 600 mg, or less than about 500 mg, or less than about 400 mg, or less than about 300 mg, or less than about 200 mg, or less than about 100 mg, or less than about 50 mg, or less than about 40 mg, or less than about 30 mg, or less than about 25 mg, or less than about 20 mg, or less than about 15 mg, or less than about 10 mg, or less than about 5 mg, or less than about 2 mg, or less than about 1 mg, or less than about 0.5 mg, and any and all whole or partial increments thereof.

In one embodiment, the present invention is directed to a packaged pharmaceutical composition comprising a container holding a therapeutically effective amount of a composition of the invention, alone or in combination with a second pharmaceutical agent; and instructions for using the composition to treat, prevent, or reduce one or more symptoms of a disease in a subject.

Routes of Administration

Routes of administration of any of the compositions of the invention include oral, nasal, rectal, parenteral, sublingual, transdermal, transmucosal (e.g., sublingual, lingual, (trans) buccal, (trans)urethral, vaginal (e.g., trans- and perivaginally), (intra)nasal, and (trans)rectal), intravesical, intrapulmonary, intraduodenal, intragastrical, intrathecal, subcutaneous, intramuscular, intradermal, intra-arterial, intravenous, intrabronchial, inhalation, and topical administration.

Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present invention are not limited to the particular formulations and compositions that are described herein.

Controlled Release Formulations and Drug Delivery Systems

Controlled- or sustained-release formulations of a pharmaceutical composition of the invention may be made using conventional technology, using for example proteins equipped with pH sensitive domains or protease-cleavable fragments. In some cases, the dosage forms to be used can be provided as slow or controlled-release of one or more active ingredients therein using, for example, hydropropylmethyl cellulose, other polymer matrices, gels, permeable membranes, osmotic systems, multilayer coatings, microparticles, liposomes, or microspheres or a combination thereof to provide the desired release profile in varying proportions. Suitable controlled-release formulations known to those of ordinary skill in the art, including those described herein, can be readily selected for use with the pharmaceutical compositions of the invention. Thus, single unit dosage forms suitable for oral administration, such as tablets, capsules, gel-caps, and caplets, which are adapted for controlled-release are encompassed by the present invention.

Most controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include extended activity of the drug, reduced dosage frequency, and increased subject compliance. In addition, controlled-release formulations can be used to affect the time of onset of action or other characteristics, such as blood level of the drug, and thus can affect the occurrence of side effects.

Most controlled-release formulations are designed to initially release an amount of drug that promptly produces the desired therapeutic effect, and gradually and continually release of other amounts of drug to maintain this level of therapeutic effect over an extended period of time. In order to maintain this constant level of drug in the body, the drug must be released from the dosage form at a rate that will replace the amount of drug being metabolized and excreted from the body.

Controlled-release of an active ingredient can be stimulated by various inducers, for example pH, temperature, enzymes, water or other physiological conditions or compounds. The term "controlled-release component" in the context of the present invention is defined herein as a compound or compounds, including, but not limited to, polymers, polymer matrices, gels, permeable membranes, liposomes, or microspheres or a combination thereof that facilitates the controlled-release of the active ingredient.

In certain embodiments, the formulations of the present invention may be, but are not limited to, short-term, rapid-offset, as well as controlled, for example, sustained release, delayed release and pulsatile release formulations.

The term sustained release is used in its conventional sense to refer to a drug formulation that provides for gradual release of a drug over an extended period of time, and that may, although not necessarily, result in substantially constant blood levels of a drug over an extended time period. The period of time may be as long as a month or more and should be a release that is longer that the same amount of agent administered in bolus form.

For sustained release, the compounds may be formulated with a suitable polymer or hydrophobic material that provides sustained release properties to the compounds. As such, the compounds for use the method of the invention may be administered in the form of microparticles, for example, by injection or in the form of wafers or discs by implantation.

In a preferred embodiment of the invention, the compounds of the invention are administered to a subject, alone or in combination with another pharmaceutical agent, using a sustained release formulation.

The term delayed release is used herein in its conventional sense to refer to a drug formulation that provides for an initial release of the drug after some delay following drug administration and that mat, although not necessarily, includes a delay of from about 10 minutes up to about 12 hours.

The term pulsatile release is used herein in its conventional sense to refer to a drug formulation that provides release of the drug in such a way as to produce pulsed plasma profiles of the drug after drug administration.

The term immediate release is used in its conventional sense to refer to a drug formulation that provides for release of the drug immediately after drug administration.

As used herein, short-term refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes and any or all whole or partial increments thereof after drug administration after drug administration.

As used herein, rapid-offset refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes, and any and all whole or partial increments thereof after drug administration.

Kits of the Invention

The invention also includes a kit comprising a compound useful within the methods of the invention and an instructional material that describes, for instance, administering the compound to a subject as a prophylactic or therapeutic treatment for cancer as described elsewhere herein. In an embodiment, the kit further comprises a (preferably sterile) pharmaceutically acceptable carrier suitable for dissolving or suspending the therapeutic composition, comprising the compound useful within the methods of the invention, for instance, prior to administering the molecule to a subject. Optionally, the kit comprises an applicator for administering the compound.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

The following examples further illustrate aspects of the present invention. However, they are in no way a limitation of the teachings or disclosure of the present invention as set forth herein.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

Example 1

Small Molecule NSC59984 Restores p53 Pathway Signaling and Anti-Tumor Effects Against Colorectal Cancer Via p73 Activation as Well as Degradation of Mutant p53 Through Effects on Hsp90 and MDM2

The tumor suppressor p53 prevents cancer development via initiating cell cycle arrest, cell death, repair, or anti-angiogenesis processes. Over 50% of human cancers harbor cancer-causing mutant p53. p53 mutations not only abrogate its tumor suppressor function, but also endow mutant p53 with a gain-of-function (GOF), creating a proto-oncogene that contributes to tumorigenesis, tumor progression and chemo- or radiotherapy resistance. Thus, targeting mutant p53 to restore a wild-type p53 signaling pathway provides an attractive strategy for cancer therapy. The results presented herein are based on the application of small molecule NSC59984 to not only restore wild-type p53 signaling, but also to deplete mutant p53 GOF. NSC59984 induces mutant p53 protein degradation via MDM2 and the ubiquitin-proteasome pathway. NSC59984 restores wild-type p53 signaling via p73 activation specifically in mutant p53-expressing colorectal cancer cells. At therapeutic doses, NSC59984 induces p73-dependent cell death in cancer cells with minimal genotoxicity and without evident toxicity towards normal cells. NSC59984 synergizes with CPT11 to induce cell death in mutant p53-expressing colorectal cancer cells and inhibits mutant p53-associated colon tumor xenograft growth in a p73-dependent manner in vivo. Without wishing to be bound by any particular theory, it is believed that specific targeting of mutant p53 may be essential for anti-cancer strategies that involve the stimulation of p73 in order to efficiently restore tumor suppression. Taken together, the data presented herein identify NSC59984 as a lead compound for anti-cancer therapy that acts by targeting GOF mutant p53 and stimulates p73 to restore the p53 pathway signaling.

The materials and methods used in these experiments are now described.

Materials and Methods

High-Throughput Screening

Functional cell-based screening for small molecules that can increase p53-transcriptional activity was performed using noninvasive bioluminescence imaging in human colorectal cancer cells (SW480, DLD-1, HCT116 and p53-null HCT116) that stably express a p53-regulated reporter, as previously described (Wang W, et al., Proc Natl Acad Sci USA 2006; 103: 11003-8). Cells were seeded in 96-well plates at a density of $5 \times 10^4$ cells/well. A dose of 10 µM of each compound from the NCI diversity set II library (1,990 compounds) was added to each well, respectively. p53 transcriptional activity was evaluated by bioluminescence imaging in cells using the IVIS imaging system (Xenogen, Alameda, Calif.) at 2, 24 and 72 hr after compound treatment, as previously described (Wang W, et al., Proc Natl Acad Sci USA 2006; 103: 11003-8). Cells treated with 5 µM of Prodigiosin were used as a positive control, and DMSO treatment was used as a negative control in each screened plate. The bioluminescence in each treatment was normalized to DMSO treatment.

Cell Lines

SW480, DLD-1, HCT116 and p53-null HCT116 cells which stably express a p53-regulated luciferase reporter were generated as previously described (Wang et al., 2006, Proc. Natl. Acad. Sci. USA 103:11003-11008; Wang et al., 2003, Cancer Biol. Ther. 2:196-202). MRC5, Wi38, Hop92 and RXF393 were obtained from ATCC and cultured as recommended. Cells were regularly authenticated by bioluminescence, growth and morphological observation.

CellTiter-Glo Luminescent Cell Viability Assay

Cells at a concentration of 5000 cells/well in 96-well plates were treated with NSC59984 or other drugs. At seventy-two hours after treatment, cells were mixed with an equal volume of CellTiter-Glo reagents (Promega, Madison, Wis.), following the manufacturer's protocol, and bioluminescence imaging was measured using the IVIS imager.

Flow Cytometry Assay

Cells were treated with NSC59984 or other drugs. Seventy-two hours after treatment, the cells were fixed with ethanol and stained with Propidium Iodide (PI). The samples were then subjected to analysis by an Epics Elite flow cytometer to measure the DNA content of the stained cells.

Knocking Down p73 Expression by Retroviral shRNA

Cells were infected with retrovirus containing the pSI-REN-REtrpcQ retroviral vector recombinant with TAp73 RNAi. Cells were cultured with blasticidin for several weeks, and blasticidin-resistant clones were selected. Knock-down of p73 was detected by measuring p73 protein levels by Western blot with anti-p73 antibody (Bethyl laboratories Inc. USA).

Over-Expression of p73 by Adenovirus Infection

Cells were infected with an adenovirus that expresses p73-beta (Ad-p73) or wild type p53 (Ad-p53) and cultured for 24 hr, as previously described (Huang C, et al., Cancer Biol Ther 2009; 8: 2186-93). Then, the infected cells were cultured in fresh medium and subjected to different treatments.

Immunoprecipitiation

Five hundred micrograms of cell lysate were incubated with 2 µg of antibody overnight at 4° C. Then, 25 µl of protein A-Sepharose beads were added to the lysates. The immunoprecipitated proteins were eluted from protein A-Sepharose beads by boiling with 2× sample buffer and subjected to SDS-PAGE.

Western Blot Analysis

Proteins were extracted from cells and electrophoresed through 4-12% SDS-PAGE then transferred to PVDF membranes. The primary antibodies indicated in the figures were incubated with the transferred PVDF in blocking buffer at 4° C. overnight. Antibody binding was detected on PVDF with appropriate IRDye-secondary antibodies (LI-COR Biosciences, USA) by the ODYSSEY infrared imaging system.

RNA Isolation and Semi-Quantitative RT-PCR (qRT-PCR)

Total RNA was isolated from cells using RNeasy mini kit (Qiagen, USA) by the recommended protocol. Reverse transcription used SuperScript II first-strand synthesis system (Invitrogen, USA) with random primers. qRT-PCR reactions used SYBR green master mix with the Real-Time PCR Detection systems (Bio-Rad, USA). Primers for qRT-PCR are (forward) 5'-GAGGTTGGCTCTGACTGTAC-3' (SEQ ID NO: 1) and (reverse) 5'-TCCGTCCCAGTAGAT-TACCA-3' (SEQ ID NO: 2) for p53, (forward) 5'-TGTC-CGTCAGAACCCATG-3' (SEQ ID NO: 3) and (reverse) 5'-AAAGTCGAAGTTCCATCGCT-3' (SEQ ID NO: 4) for p21, (forward) 5'-GACGACCTCAACGCACAGTA-3' (SEQ ID NO: 5) and (reverse) 5'-AGGAGTCCCATGAT-GAGATTGT-3' (SEQ ID NO: 6) for Puma, (forward) 5'-GCAGAGCTGGAAGTCGAGTG-3' (SEQ ID NO: 7) and (reverse) 5'-GAGCAGAAGAGTTTGGATATCAG-3' (SEQ ID NO: 8) for Noxa, (forward) 5'-CTGGGCTACACT-GAGCACC-3' (SEQ ID NO: 9) and (reverse) 5'-AAGTG-GTCGTTGAGGGCAATG-3' (SEQ ID NO: 10) for Gapdh. Target gene expression levels were normalized with Gapdh.

Colony Formation Assays

Franken N A, et al., Nat Protoc 2006; 1: 2315-9). Cancer cells were plated at 500 cells/well on 6-well plate, and then treated with NSC59984 next day. At 3 days after NSC59984 treatment, cancer cells were cultured with drug-free complete medium for two weeks with fresh medium changed every 3 days. Cells were fixed with 10% formalin and stained with 0.05% crystal violet at the end of two weeks period of cell culture.

In Vivo Anti-Tumor Assays

CRL nude mice (female, 4-6 weeks old) were inoculated s.c. in the opposite flanks with 5 million DLD-1 or p73 knock-down DLD-1 cells in an equal volume of martrigel. Treatment with NSC59984 (i.p. injection) was initiated when the tumor masses reached a size of 3-5 mm. NSC59984 (45 mg/kg) was injected by i.p. route every 5 days. Fifteen days after treatment, the mice were euthanized using an institutional animal care and use committee-approved animal protocol.

Statistical Analysis

All results were obtained from triplicate experiments, unless other indicated. Statistical analyses were performed using PRISM4 Software (GraphPad Software, Inc., San Diego, Calif., USA), ANOVA and Student's t-test. Statistical significances were determined by $p<0.05$. Combination indices were calculated using the Chou-Talalay method with CalcuSyn software (biosoft).

The results of the experiments are now described.

NSC59984 Specifically Restores p53 Pathway Signaling in Mutant p53-Expressing Human Colorectal Cancer Cells.

To identify small molecules that could restore p53 pathway signaling, approximately 1990 small molecules were screened from the National Cancer Institute (NCI) chemical diversity library II using a functional cell-based assay that was previously described (Wang W, et al., Proc Natl Acad Sci USA 2006; 103: 11003-8). Using p53-responsive bioluminescence as a readout in mutant p53-expressing cancer cells that stably express a p53 reporter, a new small molecular weight compound was found, NSC59984 (IUPAC name is (E)-1-(4-methylpiperazin-1-yl)-3-(5-nitrofuran-2yl)prop-2-en-1-one, FIG. 1A). This compound increases p53-responsive bioluminescence in SW480 cells at a concentration of 10 µM. NSC59984 was further applied to a panel of cancer cells that harbor different p53 mutations, and it was found to increase p53-responsive reporter activity, as measured as bioluminescence, in both SW480 (mutant p53 R273H, P309S) and DLD-1 (mutant p53 S241F) cells in a dose-dependent manner (1/slope=31.37 in SW480, and 29.75 in DLD1, $P<0.01$ compared to cells lacking mutant p53) (FIGS. 1B and 1C). Consistent with p53 activation, endogenous protein levels of p21, Puma, Noxa and DR5, target genes of p53 that can mediate cell cycle arrest and apoptosis, respectively, were significantly up-regulated in SW480 cells and DLD-1 cells in response to increasing doses of NSC59984 (FIG. 1E). Furthermore, mRNA levels of p21, Noxa and Puma were significantly increased in a dose-dependent manner in SW480 and DLD-1 cells at 3 hours after NSC59984 treatment (FIG. 1D). These results demonstrate that NSC59984 restores p53 pathway signaling in mutant p53-expressing SW480 and DLD1 human colorectal cancer cells. To test whether the effect of NSC59984 on restoration of the p53 pathway was mutant p53-dependent, HCT116 cells and p53-null HCT116 cells (FIG. 1) were treated with NSC59984.

Increasing doses of NSC59984 slightly induced p53-responsive bioluminescence in p53-null HCT116 cells (1/slope=102.9), and no significant increase of p53-responsive bioluminescence was observed in wild-type p53-expressing HCT116 cells (1/slope=328.4) (FIGS. 1B and 1C). Puma and p21 were not up-regulated at the mRNA level in these two cell lines, which lack mutant p53, in response to NSC59984 treatment. Noxa mRNA was slightly increased in response to 25 μM of NSC59984 in HCT116 and 12 μM of NSC59984 in p53-null HCT116 cells. However, Noxa mRNA was increased much less in these two cells than in mutant p53-expressing cancer cells DLD-1 and SW480 (FIG. 1D). Consistent with results showing lack of increase in mRNA levels of p53 target genes, protein levels of Puma, DR5 and Noxa were not up-regulated in HCT116 and p53-null HCT116 cells treated with NSC59984. Although p21 protein was up-regulated in HCT116 cells and p53-null HCT116 cells (FIG. 1E), the mRNA level of p21 was not significantly increased in response to NSC59984 treatment (FIG. 1D), suggesting that NSC59984-mediated up-regulation of p21 protein occurs at a post-translational level in HCT116 and p53-null HCT116 cells. Taken together, these results demonstrate that NSC59984 restores p53 pathway signaling specifically in mutant p53-expressing human cancer cells.

NSC59984 Induces Cell Death in Tumor Cells but Not Normal Cells with Little or No Genotoxicity.

Figure 2:
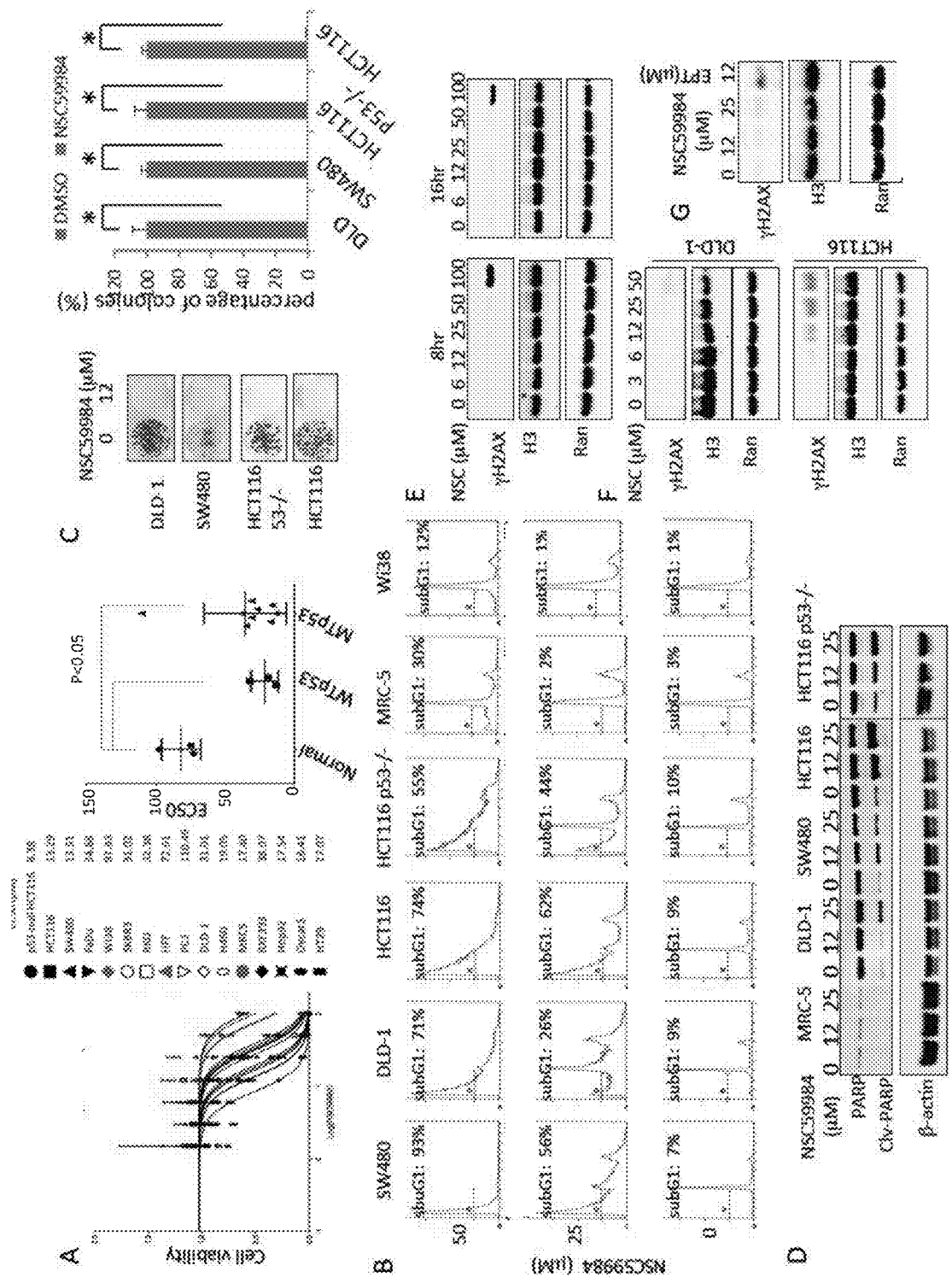
FIG. 2, comprising

The effect of NSC59984 on cell death in tumor cells was investigated because NSC59984 restores the p53 pathway in mutant p53-expressing cancer cells. EC50 values for NSC59984 were first determined in CellTiter-Glo luminescent cell viability assay using a panel of cancer cell lines bearing different p53 mutations. The EC50 of NSC59984 varied among different cancer cell lines tested, which harbor different p53 mutations. The EC50 of NSC59984 in most cancer cells was found to be significantly lower than those of normal cells (FIG. 2A). FACS analysis showed that 25 μM of NSC59984 increased the sub-G1 DNA content (26-56%) in cancer cells, but not in normal cells at 72 hr after treatment (FIG. 2B). The high dose of NSC59984 (50 μM) led to a 55-93% cancer cells to have sub-G1 content but only 12% and 30% of DNA content was found to be in Sub-G1 in Wi38 and MRC5 normal human fibroblast cells (FIG. 2B). Taken together, these data demonstrate a favorable therapeutic index between normal and cancer cells. Colony formation assays further confirmed that NSC59984 was toxic toward cancer cells. Thus, NSC59984 significantly reduced colony numbers in cancer cells (FIG. 2C). Cleaved PARP was also examined as a hallmark of caspase 3-dependent cell death in cells treated with NSC59984 for 30 hours. As shown in FIG. 2D, NSC59984 increased PARP cleavage in cancer cells in a dose-dependent manner, but PARP cleavage was not observed in normal cells at the same doses. On the basis of these findings, it was demonstrated that NSC59984 induces cell death in cancer cells but displays little or no cytotoxicity toward normal cells at the doses tested.

To determine whether NSC59984 has chemical genotoxicity that may be involved in cell death and p53 pathway restoration, the level of γH2AX, a marker of genotoxicity due to DNA double-strand breaks, was examined (Kuo L J, et al., In Vivo 2008; 22: 305-9). No γH2AX was found in SW480 and DLD-1 cancer cells treated with NSC59984 within 24 hr, even at high concentrations of 50 μM (FIG. 2E-2G). These data demonstrate that NSC59984 has little or no genotoxicity at the doses that effectively kill mutant p53-expressing cancer cells. An increase of γH2AX in HCT116 cells was observed at 8 hours after 12 μM of NSC59984 treatment.

NSC59984 Induces Mutant p53 Protein Degradation Through MDM2-Mediated Ubiquitination in Cancer Cells.

Figure 3:
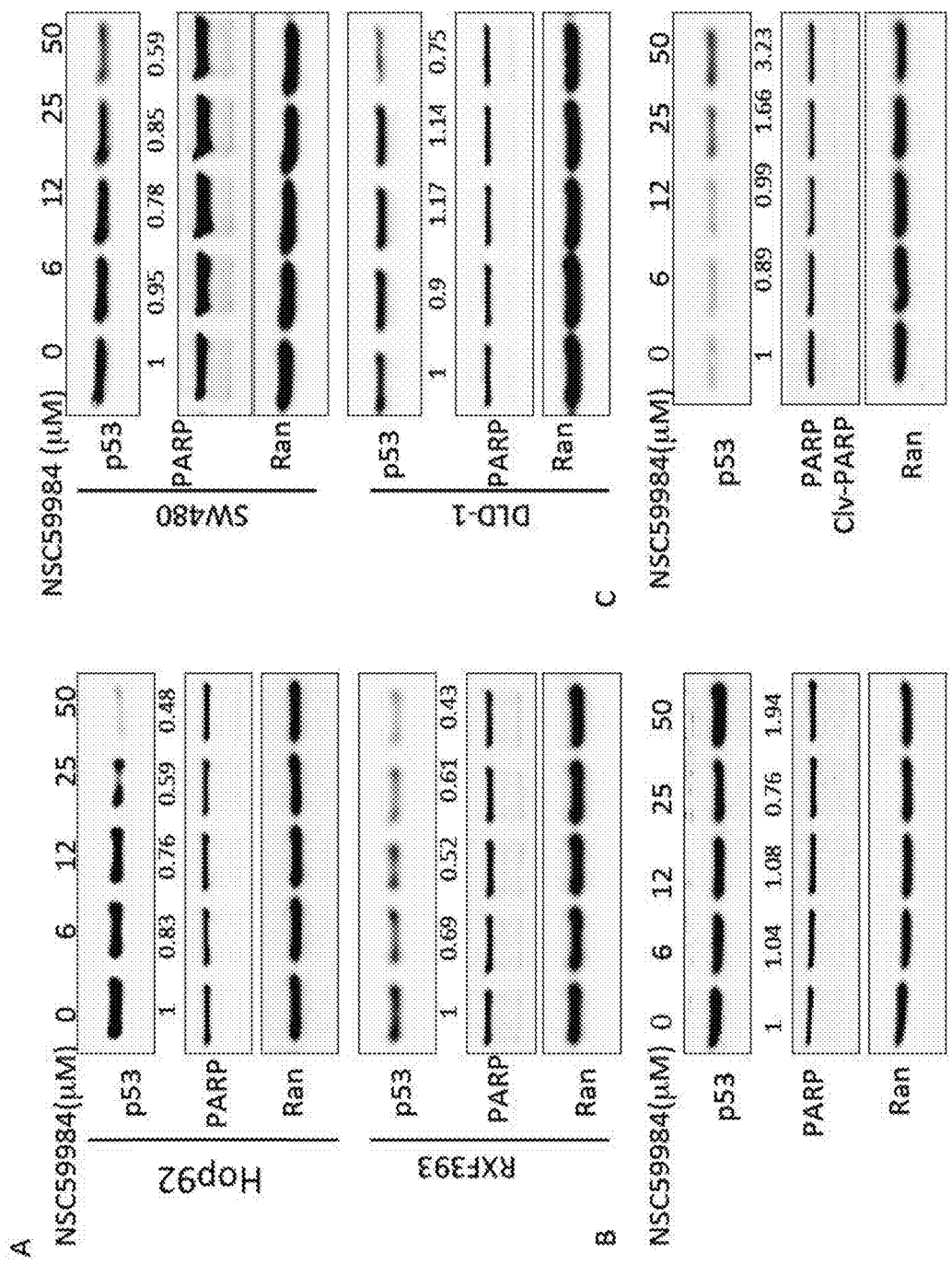
FIG. 3, comprising
Figure 8:
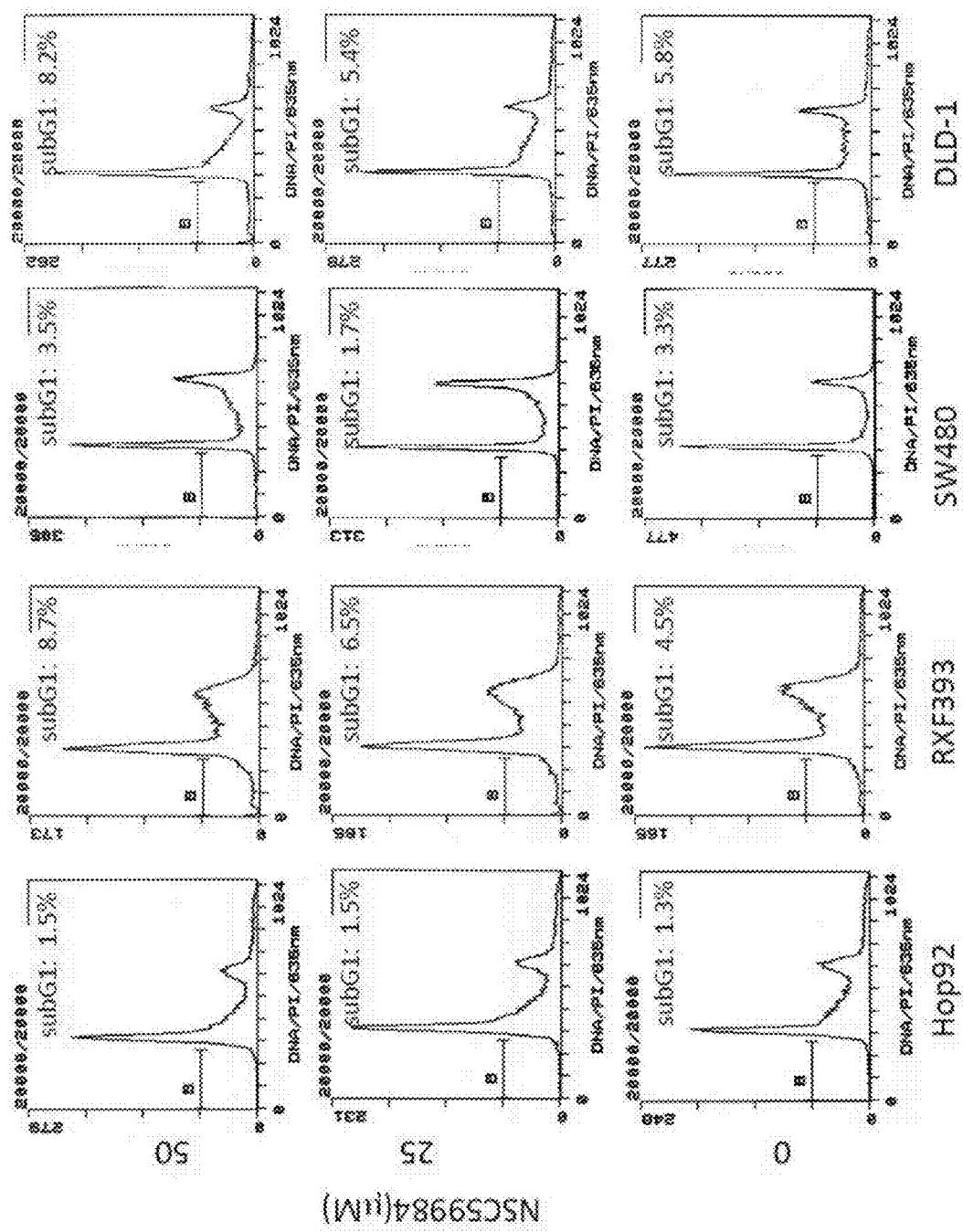
FIG. 8 depicts the results of experiments demonstrating the cell cycle profiles of Hop92, RXF393, SW480 and DLD-1 cancer cells at 8 hours after NSC59984 treatment.

Given that NSC59984 restores p53 pathway signaling specifically in mutant p53-expressing cancer cells, mutant p53 was hypothesized to be the molecular target in NSC59984-treated cancer cells. To address this issue, the effect of NSC59984 treatment on p53 protein levels was examined in a panel of human tumor cells that carry different p53 mutations, including SW480 cells (mutant p53 R273H, P309S), DLD-1 cells (mutant p53 S241F), Hop92 cells (mutant p53 R175L) and RXF393 cells (mutant p53 R175H). NSC59984 treatment down-regulated various mutant p53 proteins in these cancer cell lines in a dose-dependent manner (FIG. 3A). By contrast, wild-type p53 protein was up-regulated in MRC-5 normal cells treated with 50 μM of NSC59984 (FIG. 3B) as well as in HCT116 cancer cells treated with 25 and 50 μM of NSC59984 (FIG. 3C). The up-regulation of wild-type p53 protein was correlated with the increase of γH2AX (FIG. 2F) in HCT116 cells treated with NSC59984. These results demonstrate that NSC59984 specifically down-regulates the mutant p53 protein. Neither cleaved PARP, an early marker of cell death (FIG. 3), nor subG1 DNA-content was increased in Hop92 and SW480 cells treated with 25 μM and 50 μM of NSC59984 (FIG. 8) in the context of reduced mutant p53 protein expression. Increasing dose of NSC59984 (50 μM) slightly increased Sub-G1 DNA content to 8.7 and 8.2% from 4.5% and 5.8% of DMSO treatment in RXF393 and DLD-1cells, respectively (FIG. 8). At this dose, 25-50% of total mutant p53 protein was degraded in DLD-1 and RXF393 cells treated with NSC59984 (FIG. 3A). Taken together, these results demonstrate that cell death is not a significant mechanism by which NSC59984 reduces mutant p53. Without wishing to be bound by any particular theory, it is believed that these results exclude the possibility of cell death as a major mechanism for the NSC59984-mediated depletion of mutant p53 protein. Ubiquitination is a major mechanism by which p53 protein stability is regulated (Brooks C L, et al., Mol Cell 2006; 21: 307-15). Therefore, it was investigated whether ubiquitination is involved in the NSC59984-mediated down-regulation of mutant p53. Mutant p53-expressing cancer cells were treated with MG132, a proteasome inhibitor.

MG132 treatment rescued the NSC59984-mediated down-regulation of mutant p53 (FIG. 4A). Moreover, increased ubiquitination of mutant p53 was detected in cancer cells treated with NSC59984 and MG132 (FIG. 4C). Taken together, these results demonstrate that NSC59984 causes mutant p53 protein ubiquitination and proteasomal degradation. To further determine whether p53 transcription contributes to the NSC59984-mediated decrease of mutant p53, the mRNA level of mutant p53 was examined in SW480 cancer cells. It was found that p53 mRNA was not decreased in SW480 cells at 3 hr or at 16 hr of continuous NSC59984 treatment as compared to the DMSO control (FIG. 4D). These results taken together demonstrate that the effect of NSC59984 on decrease of mutant p53 protein occurs mostly at the post-translational level.

MDM2 is a specific E3 ubiquitin ligase that regulates p53 protein degradation (Wade M et al., Nat Rev Cancer 2013; 13: 83-96; and Brooks C L, et al., Mol Cell 2006; 21: 307-15). The aberrant accumulation of mutant p53 in cancer cells has been attributed in part to reduced MDM2 expression by the transcriptionally dysfunctional mutant p53 in the cancer cells (Oren M, et al., Cold Spring Harb Perspect Biol 2010; 2: a001107). To investigate the role of MDM2 in NSC59984-mediated mutant p53 protein degradation, mutant p53-expressing cancer cells were treated with nutlin-3, an MDM2 inhibitor. Nutlin-3 treatment partially rescued the NSC59984-induced decrease in mutant p53 (FIG. 4B). It was further found that mutant p53 was phosphorylated at Thr55 and MDM2 was phosphorylated at Ser166 in response to NSC59984 treatment in SW480 cells (FIGS. 4A and 4B). Both phosphorylation of p53 at Thr 55 and phosphorylation of MDM2 at Ser166 are important protein modifications which allow p53 degradation via MDM2 (Franken N A, et al., Nat Protoc 2006; 1: 2315-9; Li H H, et al., Mol Cell 2004; 13: 867-78; and Meek D W, et al., Mol Cancer Res 2003; 1: 1017-26). Taken together, these results demonstrate that NSC59984 induces mutant p53 protein degradation in part through an MDM2-mediated proteasomal mechanism.

Figure 9:
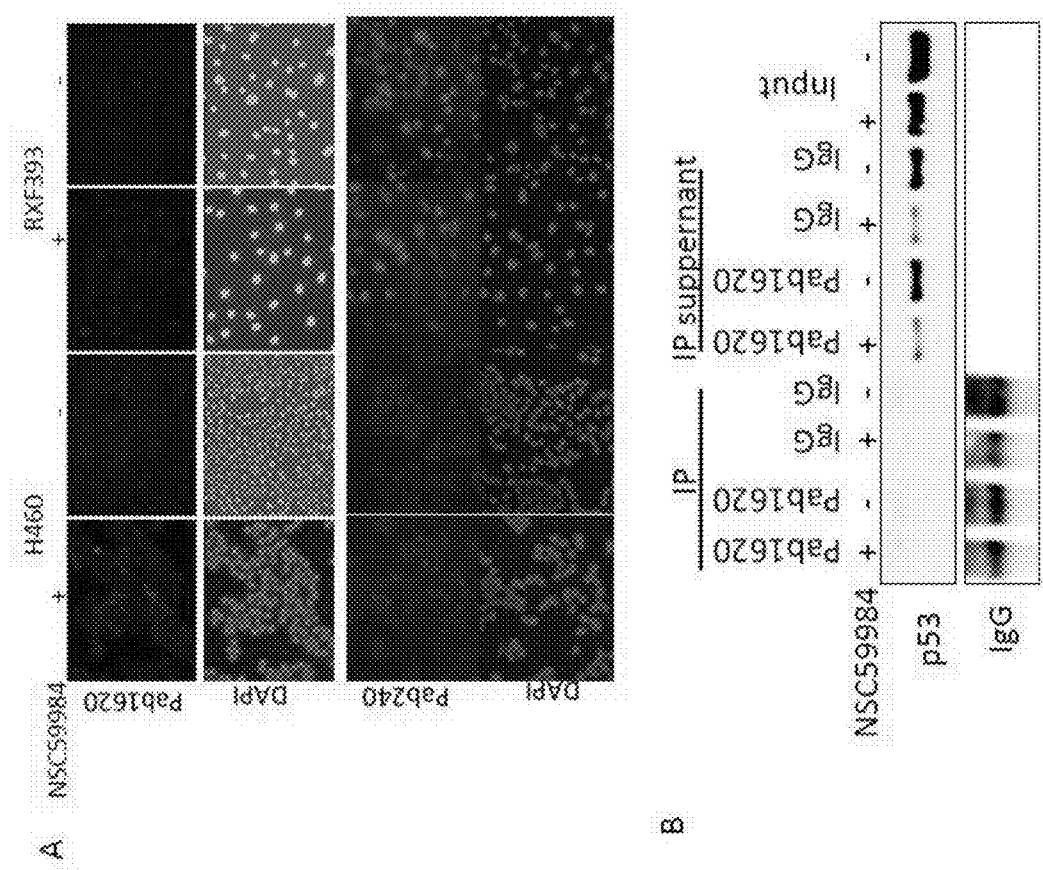
FIG. 9, comprising

To determine whether there is a wild-type conformational shift in p53 after NSC59984 treatment of mutant p53-expressing cancer cells, the wild-type p53 protein in RXF393 cells was examined using the Pab1620 antibody, which specifically recognizes a wild-type p53 protein epitope in human cells, and cells with mutant p53 do not stain as they lack the wild-type p53 epitope. RXF393 contains mutant p53 R175L, which is a mutant that has been previously examined after exposure of p53 mutant conformation modifying agents (Yu X, et al., Cancer Cell 2012; 21: 614-25). However, immunohistochemistry revealed no staining with Pab1620 in RXF393 cells before or after NSC59984 treatment. Immunoprecipitation assays further confirmed that no p53 protein bound with the Pab1620 antibody in RXF393 cell treated with NSC59984 (FIG. 9). Without wishing to be bound by any particular theory, it is believed that these results do not support a conformational shift towards wild-type of mutant p53 in cells after NSC59984 treatment, and they also exclude the possibility that mutant p53 degradation is due to a wild-type p53 conformational change. The results demonstrate that NSC59984 specifically induces mutant p53 protein degradation, at least in part, via the MDM2-mediated degradation through the ubiquitin-proteasome pathway.

NSC59984 Restores p53 Pathway Signaling Through Activation of p73.

Because mutant p53 protein is altered by NSC59984, it is possible that mutant p53 degradation leads to the release of p73 from their mutual complex. Therefore, it was hypothesized that p73 function may be stimulated in NSC59984-treated cancer cells as a mechanism to restore p53 pathway signaling. To address this issue, the effect of NSC59984 on the p53 pathway was examined in mutant p53-expressing tumor cells in which p73 was either overexpressed by adenovirus infection or constitutively knocked-down by shRNA. Overexpression of p73 was found to enhance p53-responsive reporter expression (FIG. 5A), consistent with the previous reports that p73 binds to p53 target gene promoters to stimulate transactivation (Dotsch V, et al., Cold Spring Harb Perspect Biol 2010; 2: a004887). Then, p73-overexpressing cells were further treated with NSC59984, and real-time bioluminescence imaging showed that NSC59984 treatment significantly increased p53-responsive bioluminescence interestingly to much higher levels in the p73-overexpressing SW480 cells than in the wild-type p53-overexpressing SW480 cells (FIG. 5A). NSC59984 treatment was further applied to SW480 cells in which p73 was constantly knocked-down by shRNA (FIGS. 5B and 5C). The NSC59984-induced p53-responsive bioluminescence was abrogated by knock-down of p73 (FIG. 5B). It was consistently observed that NSC59984-mediated up-regulation of endogenous of p21, Puma, DR5 and Noxa proteins was reduced by p73 knock-down (FIG. 5C). However, a small amount of p21 protein induction was still observed in p73 knock-down DLD-1 cells treated with 25 μM of NSC59984 (FIG. 5C). NSC59984 was found to up-regulate p21 expression at the protein level in HCT116 cells (FIG. 1). Without wishing to be bound by any particular theory, it is possible that p21 expression is regulated at transcriptional and protein levels in DLD-1 cells in which mRNA and protein levels of p21 were increased in response to NSC59984, although it is believed that only the transcriptional effects are p53-dependent (FIG. 1). Thus, knock-down of p73 only partially inhibited the NSC59984-mediated increase of p21 protein in DLD-1 cells (FIG. 5C). Taken together, these results demonstrate that p73 appears to be required for NSC59984 to restore the p53 pathway in mutant p53-expressing cancer cells.

NSC59984 Induces p73-Dependent Cell Apoptosis in Cancer.

Figure 6:
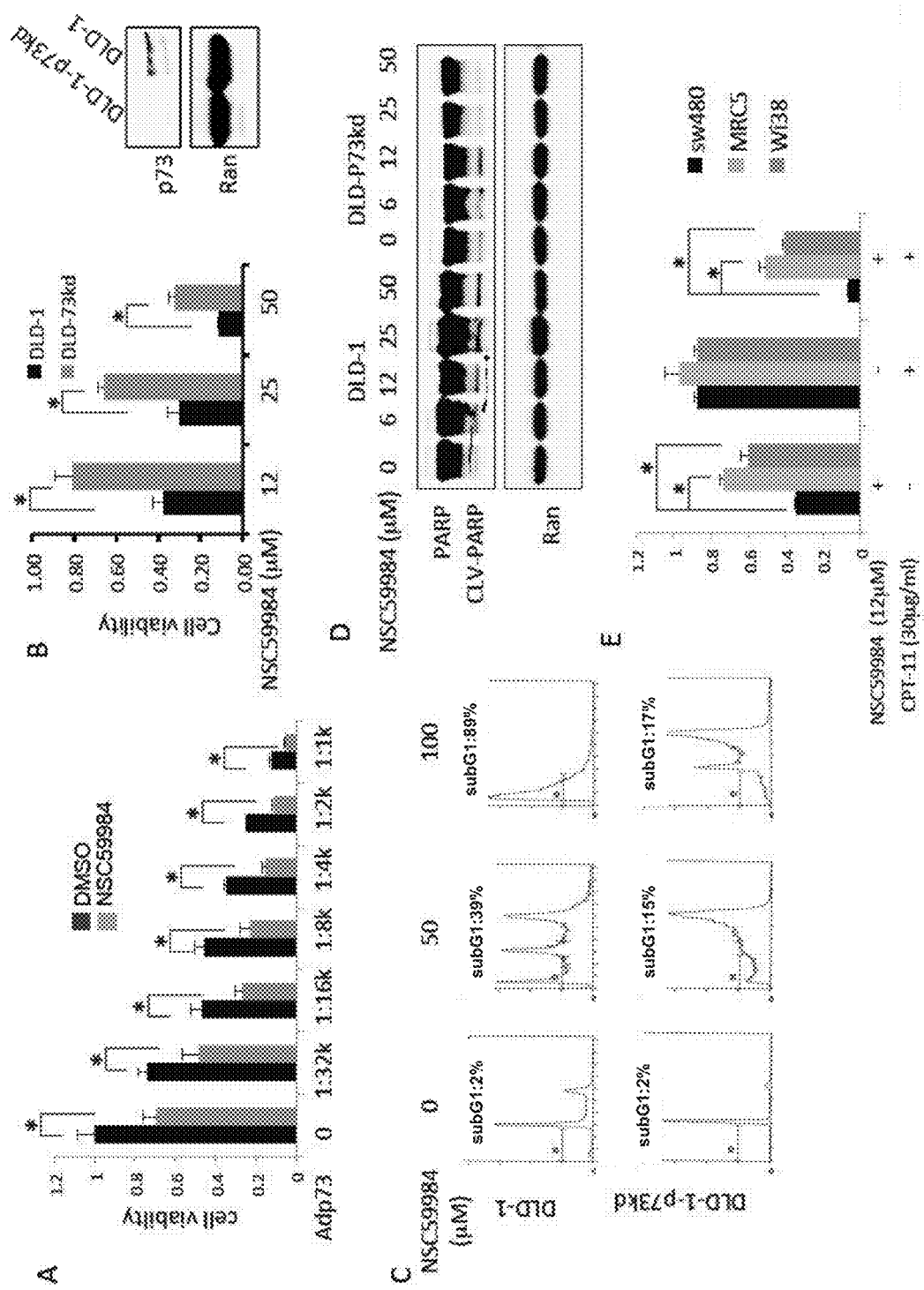
FIG. 6, comprising

Given the role of p73 in the NSC59984 restoration of the p53 pathway, the impact of p73 on NSC59984-induced cell death was next investigated. It was found that NSC59984 treatment synergized with exogenous p73 to reduce cell viability in DLD-1 cancer cells (FIG. 6A, Table 1). By contrast, cell viability in p73 knock-down DLD-1 cells was found to be higher than those in DLD-1 cells after NSC59984 treatment (FIG. 6B). FACS assays revealed that the percentage of cells with sub-G1 content was increased by NSC59984; however, the effect of NSC59984 was significantly reduced by knock-down of p73 (FIG. 6C), demonstrating that deficiency of p73 rescues cells from NSC59984-induced apoptosis. Consistent with these observations, NSC59984-induced PARP cleavage was partially abrogated by knock-down of p73 in DLD-1 cells at 24 hours of NSC59984 treatment (FIG. 6D). Taken together, these results demonstrate that NSC59984 induces p73-dependent cell death in mutant p53-expressing cancer cells.

TABLE 1

Combination indices for the NSC59984 treatment with Ad-p73 on cell viability in DLD-1 cells

| Ad-P73 (dilution) | NSC59984 (μM) | CI |
| --- | --- | --- |
| 1:32k | 12 | 0.636 |
| 1:32k | 25 | 0.282 |
| 1:32k | 50 | 0.078 |
| 1:16k | 12 | 0.239 |
| 1:16k | 25 | 0.098 |
| 1:16k | 50 | 0.027 |
| 1:8k | 12 | 0.319 |
| 1:8k | 25 | 0.115 |
| 1:8k | 50 | 0.036 |
| 1:4k | 12 | 0.303 |
| 1:4k | 25 | 0.121 |
| 1:4k | 50 | 0.037 |
| 1:2k | 12 | 0.357 |
| 1:2k | 25 | 0.127 |
| 1:2k | 50 | 0.039 |
| 1:1k | 12 | 0.273 |

TABLE 1-continued

Combination indices for the NSC59984 treatment
with Ad-p73 on cell viability in DLD-1 cells

| Ad-P73 (dilution) | NSC59984 (μM) | CI |
|---|---|---|
| 1:1k | 25 | 0.12 |
| 1:1k | 50 | 0.033 |

Combinatorial activity in DLD-1cell lines quantified in FIG. 6A was assessed by the Chou-Talalay method on cell viability. Combination index (CI)<1, =1 and >1 indicate synergism, additive effect and antagonism in drug combination treatment.

CPT11 is a DNA damaging agent used as cancer therapy in the clinic to treat colorectal cancer. CPT11 treatment has been reported to increase p73 protein levels in cancer cells (Irwin M S, et al., Cancer Cell 2003; 3: 403-10). To test whether NSC59984 mediates the cellular sensitivity to conventional chemotherapy, the combination of NSC59984 and CPT11 was applied to cancer cells and normal human fibroblast cells. There was synergic activity of combinational treatment with NSC59984 and CPT11 in SW480 colon cancer cells as well as in normal fibroblast MRC5 and Wi38cells (Table 2). Cell viability assay showed that combinational treatment with NSC59984 and CPT11 significantly reduced cell viability in SW480 cancer cells as compared to those in MRC5 and Wi38 normal cells (FIG. 6E).

TABLE 2

Combination indices for the NSC59984 and CPT-11
treatment on cell viability in cells

| CPT-11 (mg/ml) | NSC59984 (mM) | Combination index (CI) | | |
|---|---|---|---|---|
| | | MRC | Wi38 | SW480 |
| 15 | 6 | 1.06 ± 0.43 | 1.50 ± 0.18 | 3.01 ± 0.20 |
| 15 | 12 | 0.91 ± 0.21 | 1.45 ± 0.12 | 2.02 ± 0.27 |
| 15 | 25 | 0.54 ± 0.03 | 0.88 ± 0.11 | 0.66 ± 0.04 |
| 15 | 50 | 0.00 ± 0.00 | 0.03 ± 0.01 | 1.00 ± 0.02 |
| 30 | 6 | 0.75 ± 0.09 | 1.10 ± 0.14 | 1.80 ± 0.15 |
| 30 | 12 | 0.40 ± 0.07 | 0.95 ± 0.05 | 0.38 ± 0.04 |
| 30 | 25 | 0.12 ± 0.07 | 0.20 ± 0.04 | 0.65 ± 0.02 |
| 30 | 50 | 0.00 ± 0.00 | 0.03 ± 0.00 | 0.40 ± 0.04 |
| 60 | 6 | 0.49 ± 0.09 | 0.58 ± 0.10 | 0.64 ± 0.17 |
| 60 | 12 | 0.08 ± 0.04 | 0.44 ± 0.06 | 0.22 ± 0.03 |
| 60 | 25 | 0.00 ± 0.00 | 0.01 ± 0.00 | 0.57 ± 0.00 |
| 60 | 50 | 0.00 ± 0.00 | 0.05 ± 0.00 | 0.41 ± 0.04 |
| 120 | 6 | 0.06 ± 0.02 | 0.96 ± 0.22 | 0.18 ± 0.01 |
| 120 | 12 | 0.00 ± 0.00 | 0.29 ± 0.04 | 0.36 ± 0.08 |
| 120 | 25 | 0.00 ± 0.00 | 0.01 ± 0.00 | 0.62 ± 0.05 |
| 120 | 50 | 0.02 ± 0.00 | 0.11 ± 0.02 | 0.23 ± 0.04 |

SW480 cancer cells, MRC-5 and Wis38 normal fibroblast cells were treated with NSC59984 and CPT-11 for 72 hr. Combinatorial activity in cells was assessed by the Chou-Talalay method on cell viability. Combination index (CI)<1, =1 and >1 indicate synergism, additive effect and antagonism in drug combination treatment.

NSC59984 Represses Xenograft Tumor Growth In Vivo.

The potential therapeutic effects of NSC59984 was further tested in nude mice bearing colon-tumor xenografts. DLD-1 and p73 knock-down DLD-1 cells were implanted subcutaneously in the opposite flanks in each mouse. When tumor masses grew to a size of 3-5 mm in diameter, NSC59984 was administered intra-peritoneally every 5 days. NSC59984 did not cause an obvious change in mouse body weights (FIG. 7D), and no overt toxic effect of NSC59984 was observed in mice with the tested dose. NSC59984 treatment significantly repressed DLD-1 xenograft tumor growth as compared to the DMSO control (FIG. 7A). Tumor weight was further measured at day 15, the terminal point of the experiment. Tumor weight was reduced by 34% with NSC59984 treatment in DLD-1 xenograft tumors, suggesting the NSC59984 suppresses tumor growth ($p<0.05$, FIG. 7C). By contrast, tumor growth suppression was not observed in p73 knock-down DLD-1 xenograft tumors in response to NSC59984 at the same dose (FIG. 7B). NSC59984 treatment reduced tumor weight by 18% in p73 knock-down DLD-1 xenograft tumors (FIG. 7C). These results further confirm the observation in vitro that p73 is required for NSC59984 to induce tumor cell death in DLD-1 cells. Taken together, this study demonstrates that NSC59984 is a candidate compound for further evaluation as a cancer therapeutic agent.

NSC59984 has the Dual Ability to Restore the p53 Pathway and to Target Mutant p53 for Degradation.

Most small molecular weight compounds targeting mutant p53 in cancer therapy do so by either restoring the p53 pathway or by abolishing mutant p53 to remove GOF. Here, a small molecule with the dual ability to restore the p53 pathway and to target mutant p53 for degradation is reported. NSC59984 not only specifically restores the p53 pathway through p73 but also depletes mutant p53 protein in mutant p53-expressing cancer cells. p73 is demonstrated to be required for NSC59984 to restore the p53 pathway and induce cancer cell death. There are several thousand mutations of p53 that have been reported in human cancer (Olivier M, et al., Cold Spring Harb Perspect Biol 2010; 2: a001008). Mutations can have a varying effect on mutant p53 protein structure and function. Most small molecules restoring the p53 pathway have been identified and tested against a certain mutation of p53. For example, identification of Phikan083 was based on the Y222C mutation (Boeckler F M, et al., Proc Natl Acad Sci USA 2008; 105: 10360-5), SCH529074 was based on N268R mutation (38), PRIMA-1 was based on the mutations at residues 273 and 175 (Bykov V J, et al., Nat Med 2002; 8: 282-8) and NSC-319726 was based on R175H mutation (Yu X, et al., Cancer Cell 2012; 21: 614-25). Therefore, it has remained a challenge to develop universal p53-restoring drugs.

In this study, NSC59984-mediated mutant p53 protein depletion was not specific to a certain mutant p53 protein. NSC59984 was demonstrated to cause degradation of multiple mutant p53 proteins in a variety of human cancer cell lines (FIG. 3A), showing the versatility of NSC59984 to target various mutants. Importantly, NSC59984 specifically targets mutant p53 and the restoration of the p53 pathway in mutant p53-expressing cancer cells, and may also have p53 pathway-independent effects in other tumor cell lines, i.e. p21 upregulation, that may suppress their growth. It was found that NSC59984 treatment leads to the degradation of mutant p53, but not wild-type p53 protein. Wild-type p53 protein was up-regulated by NSC59984 at high doses in normal cells and cancer cells (FIGS. 3B and 3C). A corresponding effect of NSC59984 was documented to specifically restore the p53 pathway in mutant p53-expressing colorectal cancer cells, but not reactivation of the p53 pathway in tumor cells with wild-type p53 or restoration of the p53 pathway in those that are p53-null. This is based on the findings that: 1) NSC59984 increased p53-Luc reporter bioluminescence only in mutant p53-expressing cancer cells SW480 and DLD-1; 2) expression of the p53 target genes p21, Puma, DR5 and Noxa was significantly up-regulated at the mRNA and the protein levels by NSC59984 in mutant p53-expressing cancer cells SW480 and DLD-1 as compared to those in wild-type p53-expressing HCT116 and p53-null HCT116 (FIG. 1); 3) NSC59984 significantly increased p53-responsive bioluminescence to much greater levels in p73-overexpressing SW480 cells than in p53-overexpressing SW480 cancer cells (FIG. 5A). These data demonstrate the specificity of NSC59984 for targeting p53 mutant in cancer. The specificity and versatility of NSC59984 for targeting mutant p53 show that NSC59984 is a promising small molecule drug candidate for further development through targeting restoration of the p53 pathway in part through degradation of the mutant p53 protein.

Figure 4:
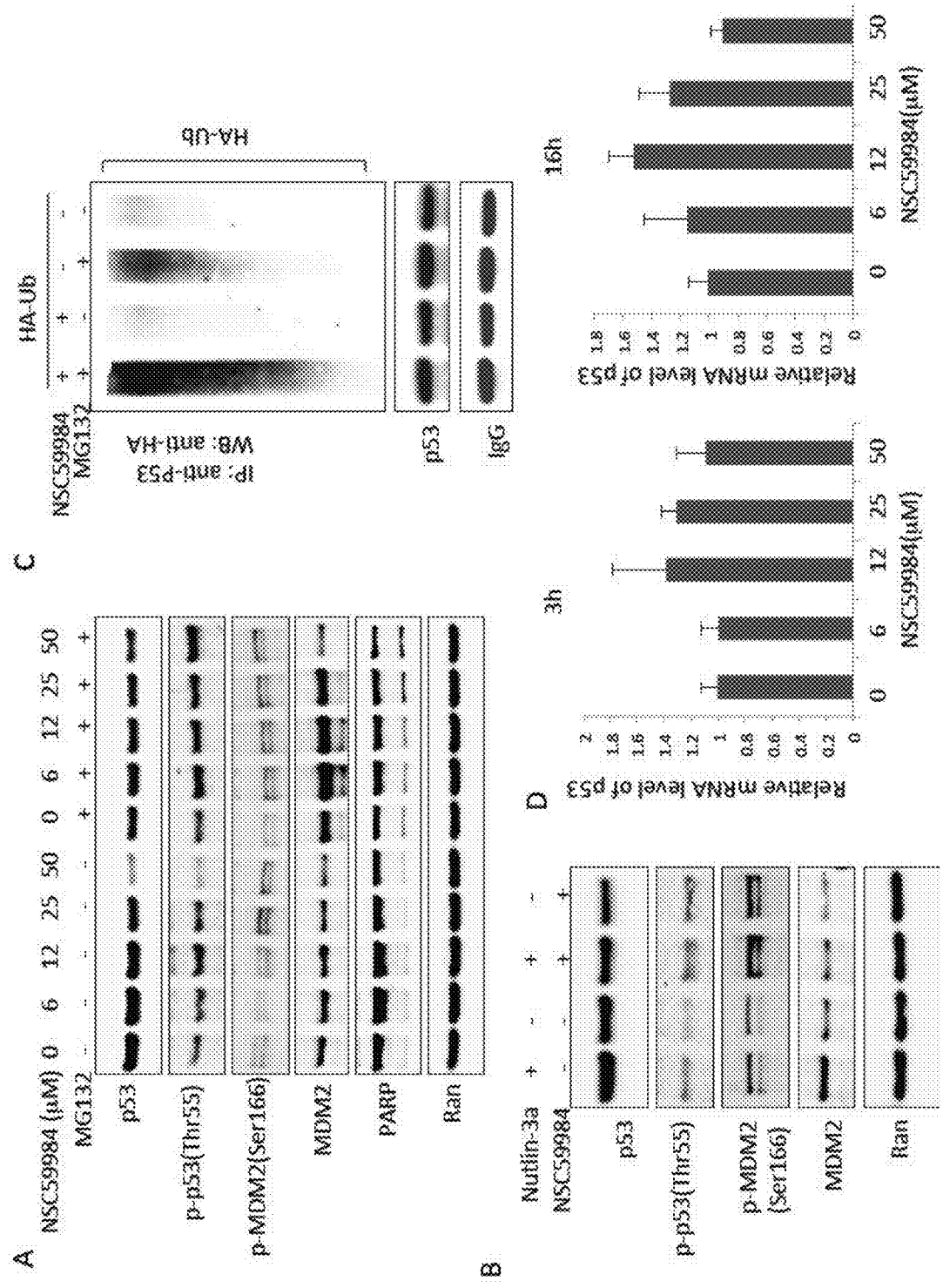
FIG. 4, comprising

The mutant p53 protein level is high in tumor cells due to its stabilization (Freed-Pastor W A, et al., Genes Dev 2012; 26: 1268-86). Stabilization of mutant p53 is mostly due to the inability of mutant p53 to interact with MDM2, an E3 ubiquitin ligase (Oren M, et al., Cold Spring Harb Perspect Biol 2010; 2: a001107). The data demonstrates that NSC59984 induces mutant p53 protein degradation via MDM2-mediated ubiquitination and proteasomal degradation (FIG. 4). Another compound, NSC319726, provided a model for the wild-type conformational change from mutant p53 to be sequentially degraded through MDM2-mediated ubiquitination (Yu X, et al., Cancer Cell 2012; 21: 614-25).

However, a wild-type p53 conformational change was not found in tumor cells treated with NSC59984 (FIG. 9) or down-regulation of wild-type p53 protein by NSC59984 treatment (FIGS. 3B and 3C). These results demonstrate that NSC59984 mediates the down-regulation of p53 due to mutant p53 degradation rather than restoration of a less stable wild-type p53 protein.

Hsp90 and hsp70 are two molecular chaperones that stabilize mutant p53 protein by affecting the MDM2-mediated turnover of mutant p53 (Peng Y, et al., J Biol Chem 2001; 276: 40583-90). Thus, mutant p53 escapes from MDM2-mediated degradation, and there are lower levels of MDM2 in mutant p53-expressing cells due to reduced transactivation of the MDM2 gene by p53 (Oren M, et al., Cold Spring Harb Perspect Biol 2010; 2: a001107). Inhibition of Hsp90 by siRNA or small molecules, such as HDACI or 17AAG, has been shown to destabilize mutant p53 through MDM2 activity (Li D, et al., Cell Death Differ 2011; 18: 1904-13; and Li D, et al., Mol Cancer Res 2011; 9: 577-88). It remained unclear whether NSC59984 induces mutant p53 protein degradation through disturbing the MDM2-hsp chaperone axis. Without wishing to be bound by any particular theory, it is believed that a conformational change of mutant p53 is another possible mechanism of mutant p53 degradation by NSC59984. For example, CP31398 induces a wild-type conformational change in mutant p53 by modifying the unfolded mutant p53 (Foster B A, et al., Science 1999; 286: 2507-10). PRIMA causes a conformational change by forming adducts with thiols in the mutant p53 core domain (Lambert J M, et al., Cancer Cell 2009; 15: 376-88). Although NSC59984 did not restore a wild-type p53 conformation, without wishing to be bound by any particular theory, it is possible that NSC59984 converts the mutant p53 structure to one more amenable to the MDM2-mediated ubiquitination to regulate mutant p53 degradation. Phosphorylation of mutant p53 at Thr 55 and phosphorylation of MDM2 at Ser166 were found in SW480 cancer cells treated with NSC59984 (FIG. 4). Phosphorylation of p53 at Thr55 and phosphorylation of MDM2 at Ser166 have been reported to contribute to p53 protein ubiquitination (Li H H, et al., Mol Cell 2004; 13: 867-78; and Meek D W, et al., Mol Cancer Res 2003; 1: 1017-26). The results demonstrate a possibility that NSC59984 induces mutant p53 and MDM2 protein modifications which contribute to mutant p53 protein degradation.

Figure 5:
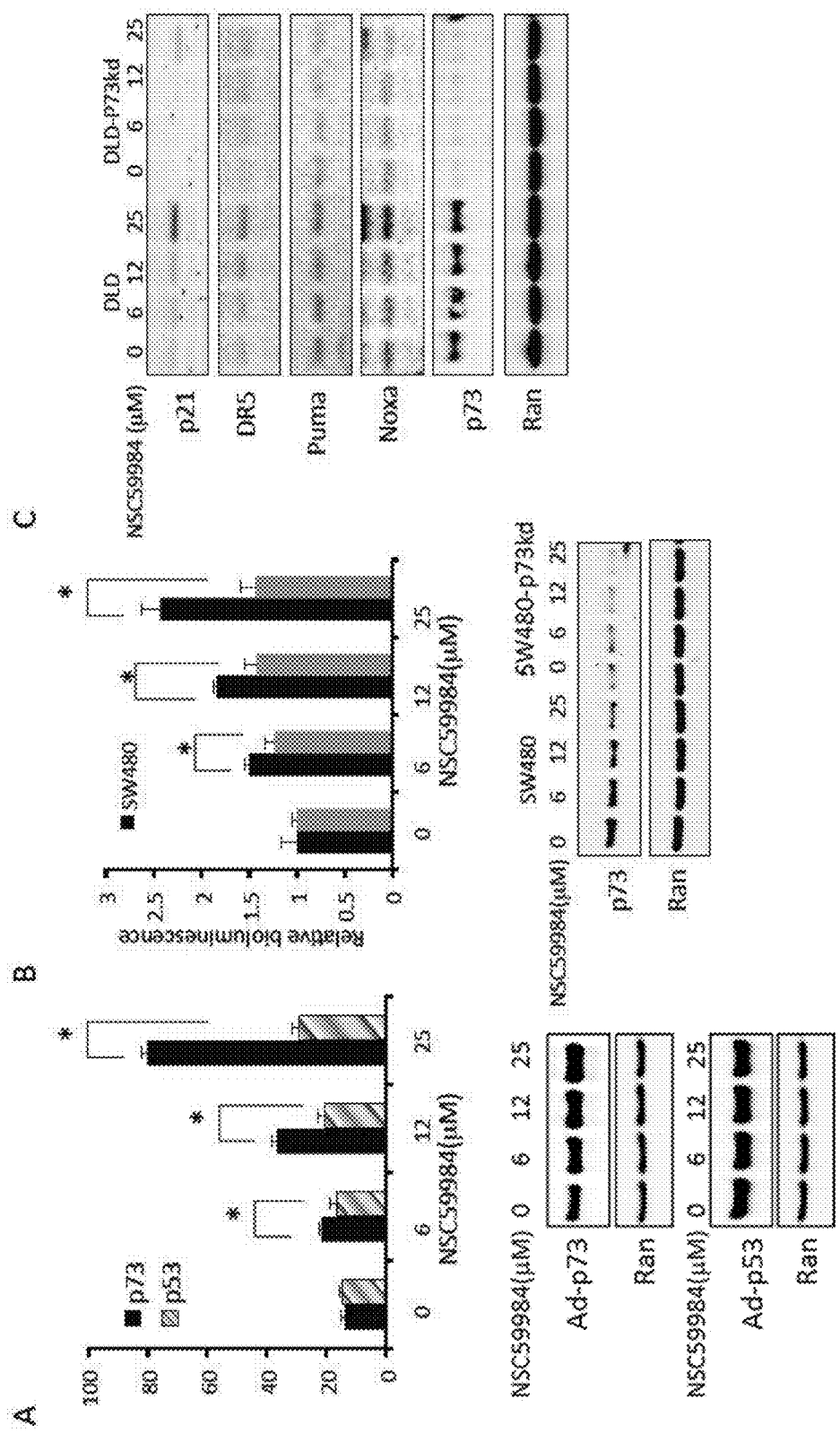
FIG. 5, comprising
Figure 7:
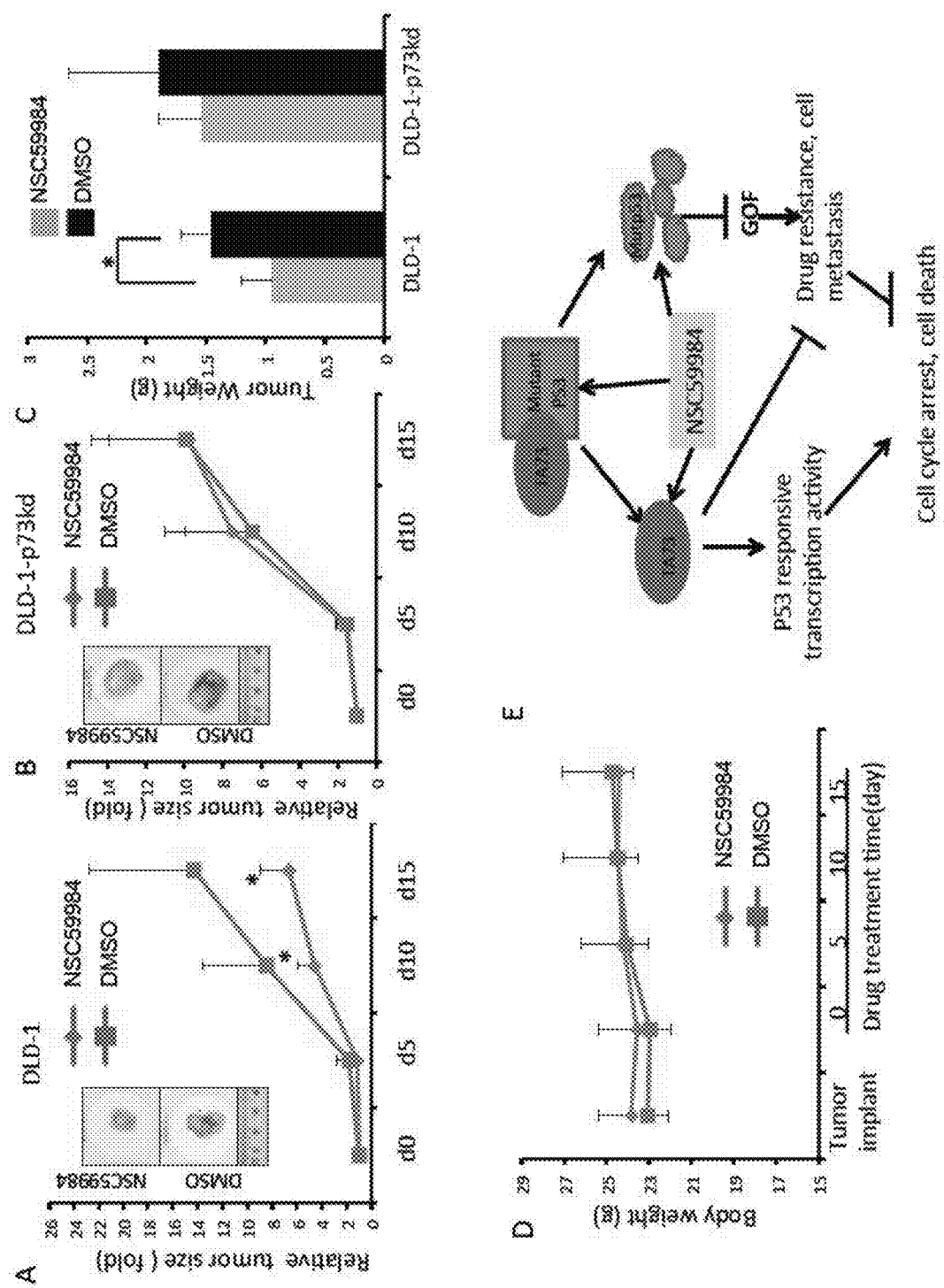
FIG. 7, comprising

Mutant p53 protein degradation is an effective means to remove its GOF, resulting in release of p73 and other factors from inhibitory complexes with mutant p53. However, many mutant p53 protein targeting small molecules, such as HDACI and 17AAG, do not restore the p53 pathway (Li D, et al., Cell Death Differ 2011; 18: 1904-13; and Li D, et al., Mol Cancer Res 2011; 9: 577-88). Unlike these mutant p53-targeting agents, NSC59984 not only degrades mutant p53 protein to release p73, but also induces p73-dependent p53 restoration (FIG. 1 and FIG. 5). Without wishing to be bound by any particular theory, it is possible that NSC59984 converts the released p73 to an active form or stabilizes p73. Active p73 functions as a transcription factor to up-regulate p53 target genes such as p21, puma and DR5. It was found that NSC59984 significantly induces p73-dependent p53 restoration only in mutant p53-expressing cancer cells (FIGS. 1 and 5), but not in p53-null or wild-type p53-expressing HCT116 cells that contain wild-type p73 (FIG. 1). These results demonstrate that restoration of the p53 pathway occurs, at least in part, through the release of p73 in mutant p53-expressing tumor cells. The fraction of released and active p73 could be increased by mutant p53 degradation. p73 protein levels were not found to be increased in the mutant p53-expressing tumor cells treated with NSC59984 at 8 hours by Western blot assay using anti-p73 antibody (Bethyl Laboratories Inc.). Without wishing to be bound by any particular theory, t is possible that post-translational modifications of p73 protein are induced by NSC59984, and that such NSC59984-mediated modifications interrupt the anti-p73 antibody (Bethyl Laboratories Inc.) recognizing modified p73 protein. It was found that NSC59984 significantly enhanced p73-dependent p53-responsive reporter bioluminescence in the p73-overexpressing cells (FIG. 5A), suggesting that active p73 is involved in NSC59984-mediated p53 restoration. p73 activity is regulated by complex post-translational modifications and protein-protein interactions. For example, p73 is activated by phosphorylation and acetylation through different signal pathways. In addition, activation of p73 is also controlled by interaction with different p73 isoforms (Conforti F, et al., Cell Death Dis 2012; 3: e285). Nevertheless, it was demonstrated that p73 is required for NSC59984 to induce cell death in addition to restoring p53 pathway. Knock-down of p73 was found to not only rescue cells from apoptosis induced by NSC59984 in vitro (FIG. 6), but also to prevent the NSC59984-mediated suppression of xenograft tumor growth in vivo (FIG. 7). Although mutant p53 deletion has been reported to be sufficient to induce cell death (Li D, et al., Cell Death Differ 2011; 18: 1904-13; and Li D, et al., Mol Cancer Res 2011; 9: 577-88), these findings demonstrate that NSC59984-induced cell death is p73-dependent in mutant p53-expressing cancer cells. Activation of p73 is an important step for p73-induced cell death (Conforti F, et al., Cell Death Dis 2012; 3: e285). Without wishing to be bound by any particular theory, it is believed that since p73 is required for both NSC59984-mediated p53 restoration and cell death, it is possible that NSC59984 induces cell death via p73-dependent restoration of the p53 pathway. Therefore, NSC59984 offers a rational bypass mechanism of p53 restoration via the activation of p73 to kill cancer cells. Based on these findings, a model is provided for NSC59984 working in cancer cells (FIG. 7E). NSC59984 releases p73 from the inhibitory complex of mutant p53 by degrading mutant p53. The released p73 may be further converted to the active form by NSC59984. Active p73 then restores the p53 pathway. NSC59984-mediated p53 restoration and/or active p73 together with depletion of GOF may result in tumor suppression (FIG. 7E).

NSC59984 induces cell death in mutant p53-expressing cancer cells with minimal genotoxicity.

Importantly, no cytotoxicity of NSC59984 was found against normal cells at the doses tested (FIG. 2), demonstrating the safety of NSC59984 administration for cancer therapy. Indeed, in vivo experiments demonstrate that i.p. injection of NSC59984 suppresses xenograft tumor growth (FIG. 7), but was not toxic toward animals, demonstrating that NSC59984 may be further evaluated for clinical development. Mutant p53 protein degradation releases many factors, including p73, from the mutant p53 protein complex (Freed-Pastor W A, et al., Genes Dev 2012; 26: 1268-86), which might result in p73 independent off-target effects. Because of the specificity of NSC59984 for mutant p53, the potential off-target effects may be limited in mutant p53-expressing cells and may not affect normal cells containing wild-type p53. However, the anti-tumor effect of NSC59984 on cancer cells is not limited in p53-mutant cancer cells (FIG. 1). It is noted that NSC59984 induced cell apoptosis in wild-type p53-expressing as well as p53-null cancer cells, demonstrating that the cell death induced by NSC59984 in these cell lines is p53-independent. It is possible there may be tumor suppressive effects due to NSC59984-mediated up-regulation of p21 protein in these two cell lines (FIG. 1). These findings demonstrate that NSC59984 regulates p21 expression at the post-translational level in HCT116 and p53-null HCT116 cancer cells. p21 regulation at the post-translational level could be an off-target effect of NSC59984 in cancer cells.

p73 is an important determinant of chemosensitivity. In response to cellular stresses and DNA damage, p73 is activated through different signaling pathways and enhances chemosensitivity (Conforti F, et al., Cell Death Dis 2012; 3: e285; and Irwin M S, et al., Cancer Cell 2003; 3: 403-10). However, mutant p53 inhibits p73 activation, resulting in drug resistance. The finding that NSC59984 rescues p73 activity to restore the p53 pathway provides a potential application of NSC59984 to reduce chemoresistance. Indeed, NSC59984 synergizes with CPT11 to suppress colorectal cancer cell growth (FIG. 6E, Table 2). Therefore, NSC59984 warrants further evaluation in combination therapy to reduce the dose of CPT11 required for growth suppression in colorectal cancer. Combinatorial treatment with NSC59984 may minimize the side effects of CPT11 chemotherapy and increase its anti-tumor effects in colorectal cancer patients. Taken together, these results demonstrate that NSC59984 is a candidate therapeutic as both a single agent or in combination with conventional chemotherapy. Based on the findings in this study, NSC59984 is a promising drug candidate that specifically targets mutant p53 via a mechanism involving both mutant p53 depletion and p73-dependent p53 pathway restoration.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of treating colon cancer in a subject comprising administering to the subject an effective amount of a pharmaceutical composition comprising a pharmaceutically acceptable carrier and a compound of formula (I) or a salt, solvate, or N-oxide thereof:

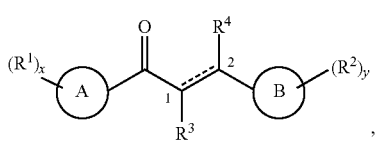

wherein in formula (I):
ring A is a bicyclic aryl, a monocyclic or bicyclic heteroaryl, or a monocyclic or bicyclic heterocyclyl ring, and wherein the aryl, heteroaryl, or heterocyclyl ring is optionally substituted with 0-5 $R^1$ groups;
ring B is a monocyclic or bicyclic aryl, a monocyclic or bicyclic heteroaryl, or a monocyclic or bicyclic heterocyclyl ring, and wherein the aryl, heteroaryl, or heterocyclyl ring is optionally substituted with 0-5 $R^2$ groups;
the bond between carbon 1 and carbon 2 is either a single bond or a double bond;
each occurrence of $R^1$ and $R^2$ are independently selected from the group consisting of —$C_1$-$C_6$ alkyl, —$C_1$-$C_6$ fluoroalkyl, —$C_1$-$C_6$ heteroalkyl, F, Cl, Br, I, —CN, —$NO_2$, —$OR^5$, —$SR^5$, —S(=O)$R^5$, —S(=O)$_2R^5$, —NHS(=O)$_2R^5$, —C(=O)$R^5$, —OC(=O)$R^5$, —CO$_2R^5$, —OCO$_2R^5$, —CH($R^5$)$_2$, —N($R^5$)$_2$—, —C(=O)N($R^5$)$_2$—, —OC(=O)N($R^5$)$_2$, —NHC(=O)NH($R^5$), —NHC(=O)$R^5$, —NHC(=O)O$R^5$, —C(OH)($R^5$)$_2$, and —C($NH_2$)($R^5$)$_2$;
$R^3$ and $R^4$ are each independently selected from the group consisting of H or $C_1$-$C_6$ alkyl, wherein the alkyl group is optionally substituted with 0-5 $R^1$ groups;
each occurrence of $R^5$ is independently selected from the group consisting of H or $C_1$-$C_6$ alkyl, wherein the alkyl group is optionally substituted;
x is an integer from 0 to 5; and
y is an integer from 0 to 5, wherein the colon cancer is associated with a p53 gain of function (GOF) mutation.

2. The method of claim 1, wherein ring A is a monocyclic heterocyclyl ring.

3. The method of claim 1, wherein ring A is piperazinyl.

4. The method of claim 1, wherein ring A is 4-methyl piperazinyl.

5. The method of claim 1, wherein ring B is a monocyclic heteroaryl ring.

6. The method of claim 1, wherein ring B is a 5- or 6-membered heterocyclyl or heteroaryl ring.

7. The method of claim 6, wherein the heterocyclyl or heteroaryl ring has one heteroatom, wherein the heteroatom is alpha to the linkage between ring B and carbon 2.

8. The method of claim 1, wherein ring B is furyl.

9. The method of claim 1, wherein ring B is 5-nitrofuryl.

10. The method of claim 1, wherein $R^3$ and $R^4$ are each hydrogen.

11. The method of claim 1, wherein ring A has 1 to 2 ring heteroatoms.

12. The method of claim 1, wherein at least one of $R^2$ is selected from the group consisting of F, Cl, Br, I, —CN, —$NO_2$, —C(=O)$R^5$, —CO$_2R^5$, —S(=O)$R^5$, and —S(=O)$_2R^5$.

13. The method of claim 1, wherein the bond between carbon 1 and carbon 2 is a double bond.

14. The method of claim 1, wherein the compound of formula (I) is (E)-1-(4-methylpiperazin-1-yl)-3-(5-nitrofuran-2-yl)prop-2-en-1-one (NSC59984)

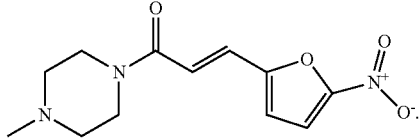

15. The method of claim 1, further comprising administering another therapy to the subject.

16. The method of claim 15, wherein the other therapy is selected from the group consisting of radiation therapy, chemotherapy, and a combination thereof.

17. The method of claim 16, wherein the other therapy is administered to the subject at a lower level compared to the level when administered in the absence of the compound.

* * * * *